United States Patent
Song et al.

(10) Patent No.: US 12,171,876 B2
(45) Date of Patent: Dec. 24, 2024

(54) CATIONIC LIPID COMPOUND, COMPOSITION CONTAINING SAME AND USE THEREOF

(71) Applicant: HANGZHOU TIANLONG PHARMACEUTICAL CO., LTD., Hangzhou (CN)

(72) Inventors: Gengshen Song, Hangzhou (CN); Huanyu Wang, Hangzhou (CN); Hognlei Zhang, Hangzhou (CN); Xichao Chen, Hangzhou (CN); Xiaowen Yu, Hangzhou (CN); Dawei Huang, Hangzhou (CN)

(73) Assignee: HANGZHOU TIANLONG PHARMACEUTICAL CO., LTD., Hangzhou (CN)

( * ) Notice: Subject to any disclaimer, the term of this patent is extended or adjusted under 35 U.S.C. 154(b) by 0 days.

(21) Appl. No.: 18/565,894

(22) PCT Filed: Jan. 27, 2022

(86) PCT No.: PCT/CN2022/074153
§ 371 (c)(1),
(2) Date: Nov. 30, 2023

(87) PCT Pub. No.: WO2023/133946
PCT Pub. Date: Jul. 20, 2023

(65) Prior Publication Data
US 2024/0252435 A1   Aug. 1, 2024

(30) Foreign Application Priority Data
Jan. 13, 2022 (CN) .......................... 202210034449.4

(51) Int. Cl.
| | | |
|---|---|---|
| A61K 9/127 | (2006.01) |
| A61K 9/51 | (2006.01) |
| A61K 31/7105 | (2006.01) |
| A61K 45/06 | (2006.01) |
| C07C 229/16 | (2006.01) |

(52) U.S. Cl.
CPC .......... *A61K 9/1271* (2013.01); *A61K 9/5123* (2013.01); *A61K 31/7105* (2013.01); *A61K 45/06* (2013.01); *C07C 229/16* (2013.01)

(58) Field of Classification Search
CPC ................ A61K 9/1271; A61K 9/5123; A61K 31/7105; A61K 45/06; C07C 229/16
See application file for complete search history.

(56) References Cited

U.S. PATENT DOCUMENTS

| | | | |
|---|---|---|---|
| 2005/0222064 A1 | 10/2005 | Vargeese et al. | |
| 2018/0273467 A1 | 9/2018 | Benenato | |
| 2019/0314292 A1* | 10/2019 | Benenato | .............. C07C 251/38 |

FOREIGN PATENT DOCUMENTS

| | | | | |
|---|---|---|---|---|
| CN | 102625696 B | 6/2015 | | |
| CN | 108368028 A | 8/2018 | | |
| CN | 109195621 A | 1/2019 | | |
| CN | 110352071 A | 10/2019 | | |
| CN | 110520409 A | 11/2019 | | |
| CN | 113387825 A | 9/2021 | | |
| CN | 114044741 A | 2/2022 | | |
| JP | 2022501360 A | 1/2022 | | |
| WO | 2020061367 A1 | 3/2020 | | |
| WO | WO-2021030701 A1 * | 2/2021 | ......... A61K 31/7088 |
| WO | 2021142280 A1 | 7/2021 | | |

OTHER PUBLICATIONS

Coelho et al., "Safety and efficacy of RNAi therapy for transthyretin amyloidosis," N Engl J Med (2013) vol. 369, pp. 819-829.
Berge et al. "Pharmaceutical Salts," J Pharm Sci (1977) vol. 66, pp. 1-19.
International Search Report issued in PCT/CN2022/074153, mailed Mar. 30, 2022.

* cited by examiner

*Primary Examiner* — Robert A Wax
*Assistant Examiner* — John W Lippert, III
(74) *Attorney, Agent, or Firm* — K&L Gates LLP

(57) ABSTRACT

Provided in the present disclosure are a compound of formula (I), or an N-oxide, solvate, pharmaceutically acceptable salt or stereoisomer thereof. Further provided are a composition containing the aforementioned compound, and the use thereof in the delivery of a therapeutic agent or prophylactic agent.

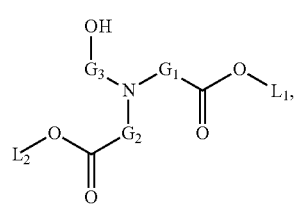

32 Claims, 5 Drawing Sheets

CATIONIC LIPID COMPOUND, COMPOSITION CONTAINING SAME AND USE THEREOF

This application is a U.S. National Phase Application under 35 U.S.C. § 371 of International Application No. PCT/CN2022/074153, filed Jan. 27, 2022, which claims priority to Chinese patent application No. 202210034449.4 filed on Jan. 13, 2022, the contents of which are incorporated herein by reference as part of the present application.

TECHNICAL FIELD

The present disclosure belongs to the field of medicine. The present disclosure specifically relates to a cationic lipid compound, a composition containing the same and uses thereof.

BACKGROUND OF THE INVENTION

Effective targeted delivery of biologically active substances such as small molecule drugs, peptides, proteins and nucleic acids, especially nucleic acids, is a persistent medical problem. Nucleic acid therapeutics face great challenges due to low cell permeability and high susceptibility to degradation of certain nucleic acid molecules, including RNA.

Compositions, liposomes and liposome complexes (lipoplexes) containing a cationic lipid have been demonstrated as delivery carriers to effectively deliver biologically active substances, such as small molecule drugs, polypeptides, proteins and nucleic acids, into cells and/or intracellular compartments. These compositions generally comprise one or more "cationic" and/or amino (ionizable) lipids, and also comprise a neutral lipid, a structured lipid, and a polymer-conjugated lipid. Cationic and/or ionizable lipids include, for example, amine-containing lipids that can be readily protonated. Although a variety of such lipid-containing nanoparticle compositions have been demonstrated, safety, efficacy and specificity remain to be improved. Notably, the increased complexity of lipid nanoparticles (LNPs) complicates their production and may increase their toxicity, which is a major concern that could limit their clinical application. For example, LNP siRNA particles such as patisiran require preadministration of steroids and antihistamines to eliminate unwanted immune responses (T. Coelho, D. Adams, A. Silva, et al., Safety and efficacy of RNAi therapy for transthyretin amyloidosis, N Engl J Med, 369 (2013) 819-829). Accordingly, there is a need to develop improved cationic lipid compounds, and compositions comprising the same, that facilitate the delivery of therapeutic and/or prophylactic agents such as nucleic acids to cells.

SUMMARY OF THE INVENTION

The present disclosure is based at least on the discovery that there is no apparent correspondence between the structure of cationic lipid compounds and intracellular transfection efficiency, cytotoxicity, and high and sustained expression in animals. Compounds with small structural differences may have very large differences in transfection efficiency and/or cytotoxicity and high expression in cells. For example, compounds YK-009 and YK-010 of this application have nearly 60 times difference in cell transfection efficiency, and 25% or more of difference in toxicity to transfected cells. For another example, the difference in the expression and sustained expression of compounds YK-003 and YK-010 in mice can be 50 times.

Therefore, it is very difficult to screen out suitable cationic lipid compounds that can simultaneously have high transfection efficiency and low cytotoxicity, and high expression and sustained expression in mice. Through unique design, the present disclosure discovered some compounds such as YK-009, YK-003, YK-006, YK-008 and YK-011, which can deliver nucleic acids with high cell transfection efficiency, low or no cytotoxicity, and high and sustained expression in animals compared with other compounds in the prior art, and achieve unexpected technical effects.

One aspect of the present disclosure provides a novel cationic lipid compound, which is a compound of formula (I)

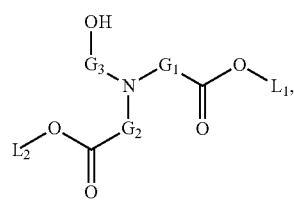

or an N-oxide, solvate, pharmaceutically acceptable salt or stereoisomer thereof, wherein: $G_1$ is $C_{1-6}$ alkylene, preferably unsubstituted $C_{2-5}$ alkylene, more preferably unsubstituted $C_3$ alkylene; $G_2$ is $C_{2-8}$ alkylene, preferably unsubstituted $C_{4-6}$ alkylene, more preferably unsubstituted $C_5$ alkylene; $G_3$ is $C_{1-3}$ alkylene, preferably unsubstituted $C_2$ alkylene; $L_1$ is $C_{6-15}$ linear alkyl, preferably unsubstituted $C_{8-12}$ linear alkyl, more preferably unsubstituted $C_{10}$ linear alkyl; $L_2$ is $C_{12-25}$ branched alkyl, preferably unsubstituted $C_{14-22}$ branched alkyl, more preferably unsubstituted $C_{18}$ branched alkyl. For example, $L_2$ is:

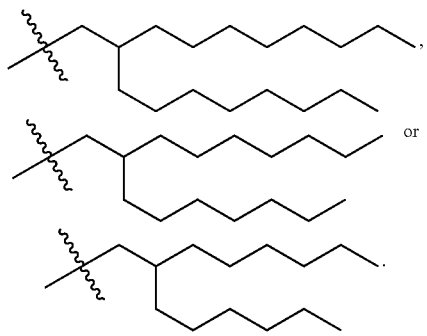

For example, the compound of formula (I) has one of the following structures:

YK-001

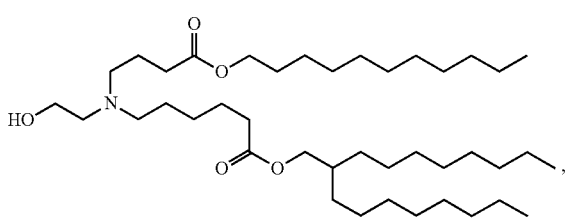

YK-002

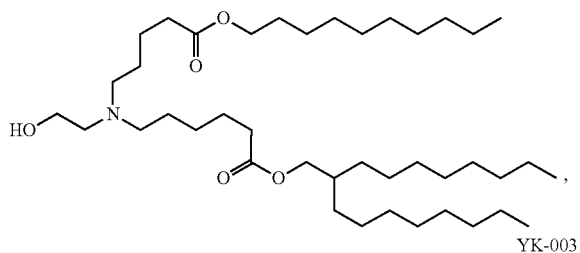

YK-003

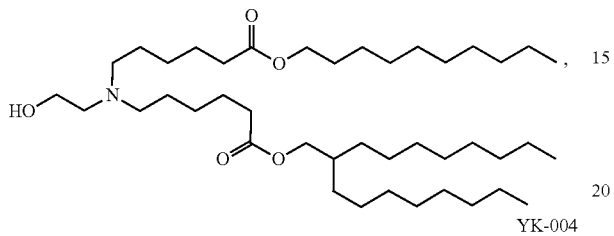

YK-004

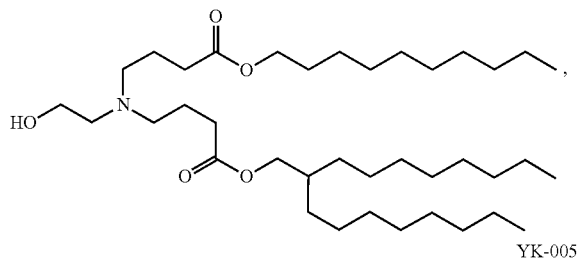

YK-005

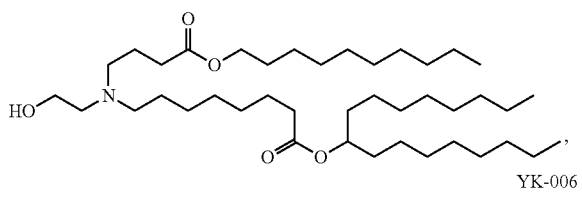

YK-006

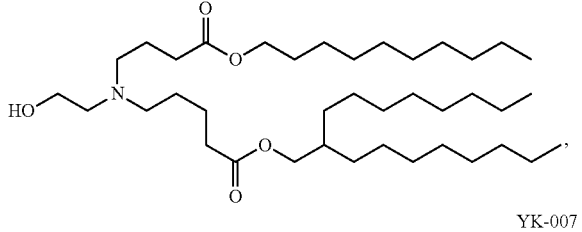

YK-007

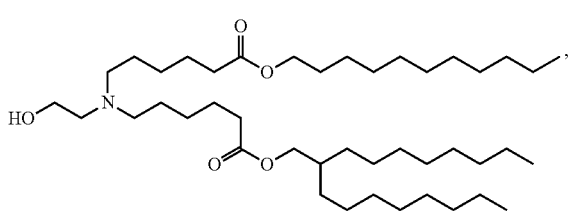

YK-008

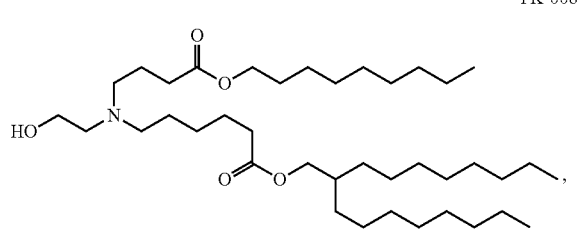

YK-009

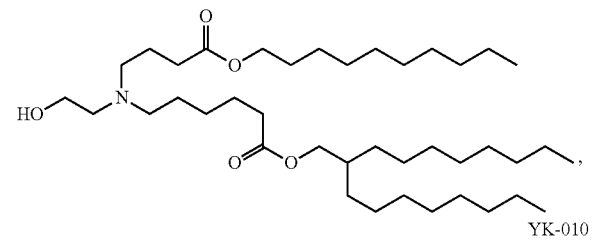

YK-010

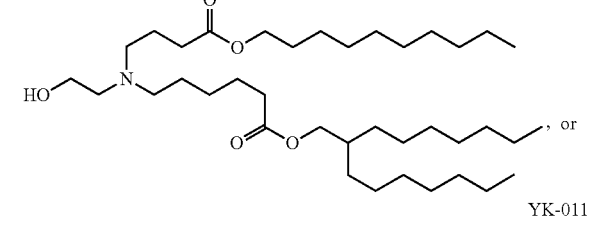

, or

YK-011

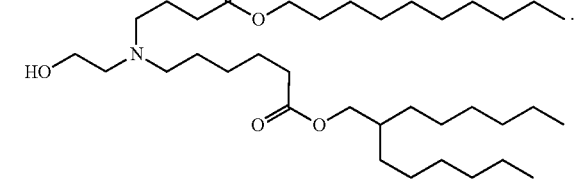

.

Another aspect of the present disclosure provides a composition containing a carrier comprising the cationic lipid described above.

For example, the molar ratio of the cationic lipid to the carrier is from 30% to 70%.

In one embodiment, the carrier further comprises a neutral lipid. For example, the molar ratio of the cationic lipid to the neutral lipid is from 1:1 to 10:1.

In one embodiment, the neutral lipid comprises one or more of phosphatidylcholine, phosphatidylethanolamine, sphingomyelin, ceramide, sterol and derivatives thereof.

For example, the neutral lipid is selected from one or more of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoyl phosphatidylglycerol (DPPG), palmitoyl oleoyl phosphatidylethanolamine (POPE), distearoyl-phosphatidyl-ethanolamine (DSPE), dipalmitoyl phosphatidylethanolamine (DPPE), dimyristoyl phosphoethanolamine (DMPE), 1-stearyl-2-oleoyl-stearoylethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyl oleoyl phosphatidylcholine, lysophosphatidylcholine, lysophosphatidylethanolamine (LPE), and mixtures thereof.

In a preferred embodiment, the neutral lipid is DOPE and/or DSPC.

In one embodiment, the carrier further comprises a structured lipid. For example, the molar ratio of the cationic lipid to the structured lipid is from 1:1 to 5:1.

In one embodiment, the structured lipid is selected from one or more of cholesterol, nonsterol, sitosterol, ergosterol, campesterol, stigmasterol, brassicasterol, tomatine, tomatine, ursolic acid, alpha-tocopherol, and corticosteroid. In a preferred embodiment, the structured lipid is cholesterol.

In one embodiment, the carrier further comprises a polymer-conjugated lipid. For example, the molar ratio of the polymer-conjugated lipid to the carrier is from 0.5% to 5%.

In one embodiment, the polymer-conjugated lipid is selected from one or more of PEG-modified phosphatidylethanolamine, PEG-modified phosphatidic acid, PEG-modified ceramide, PEG-modified dialkylamine, PEG-modified diacylglycerol, and PEG-modified dialkylglycerol.

For example, the polymer-conjugated lipid is selected from one or more of distearoylphosphatidylethanolamine polyethylene glycol 2000 (DSPE-PEG2000), dimyristoylglycero-3-methoxy polyethylene glycol 2000 (DMG-PEG2000) and methoxypolyethylene glycol ditetradecylacetamide (ALC-0159).

In one embodiment, the carrier includes a neutral lipid, a structured lipid, and a polymer-conjugated lipid, wherein the molar ratio of the cationic lipid, the neutral lipid, the structured lipid, and the polymer-conjugated lipid is (25~65):(5~25):(25~45):(0.5~5), is preferably 50:10:38.5:1.5.

In one embodiment, the composition is a nanoparticle formulation, and the average particle size of the nanoparticle formulation is from 10 nm to 210 nm, preferably from 100 nm to 205 nm; the polydispersity coefficient of the nanoparticle formulation is ≤50%, preferably ≤30%.

In one embodiment, the cationic lipid further comprises one or more other ionizable lipid compound(s).

In one embodiment, the composition further comprises a therapeutic or prophylactic agent. For example, the mass ratio of the carrier to the therapeutic or prophylactic agent in the composition is from 10:1 to 30:1.

In one embodiment, the mass ratio of the carrier to the therapeutic or prophylactic agent is from 15:1 to 25:1, is preferably 16:1.

In one embodiment, the therapeutic or prophylactic agent comprises one or more of nucleic acid molecules, small molecule compounds, polypeptides or proteins.

For example, the therapeutic or prophylactic agent is a vaccine or compound capable of eliciting an immune response.

In one embodiment, the therapeutic or prophylactic agent is a nucleic acid. For example, the therapeutic or prophylactic agent may be deoxyribonucleic acid (DNA).

In one embodiment, the therapeutic or prophylactic agent is ribonucleic acid (RNA).

In one embodiment, the RNA is selected from the group consisting of small interfering RNA (siRNA), asymmetric interfering RNA (aiRNA), microRNA (miRNA), Dicer-substrate RNA (dsRNA), small hairpin RNA (shRNA), messenger RNA (mRNA), and mixtures thereof. For example, the RNA is mRNA.

In one embodiment, the composition further includes one or more of pharmaceutically acceptable excipients or diluents.

Another aspect of the present disclosure provides the above cationic lipid or composition for use in delivering a therapeutic or prophylactic agent to a patient in need thereof.

Another aspect of the present disclosure provides a use of the above cationic lipid or composition in the manufacture of nucleic acid medicine, gene vaccine, small molecule medicine, polypeptide or protein medicine.

Another aspect of the present disclosure provides a use of the above cationic lipid or composition in the manufacture of a medicament for treating a disease or condition in a mammal in need thereof.

Another aspect of the present disclosure provides the above cationic lipid or composition for use in treating a disease or condition in a mammal in need thereof.

Another aspect of the present disclosure provides a method for treating or preventing a disease or condition, comprising administering a therapeutically or prophylactically effective amount of the above composition to a patient or subject in need thereof.

In one embodiment, the disease or condition is characterized by dysfunctional or abnormal protein or polypeptide activity.

For example, the disease or condition is selected from the group consisting of infectious diseases, cancer and proliferative diseases, genetic diseases, autoimmune diseases, diabetes, neurodegenerative diseases, cardiovascular and renovascular diseases and metabolic diseases.

For example, the infectious disease is selected from diseases caused by coronavirus, influenza virus or HIV virus, infantile pneumonia, Rift Valley fever, yellow fever, rabies, and various herpes.

In a preferred embodiment, the mammal is a human.

In one embodiment, the composition is administered intravenously, intramuscularly, intradermally, subcutaneously, intranasally or by inhalation. For example, the composition is administered subcutaneously.

In one embodiment, the therapeutic or prophylactic agent is administered to the mammal at a dose of about 0.001 mg/kg to about 10 mg/kg.

BRIEF DESCRIPTION OF THE DRAWINGS

In order to illustrate the technical solutions of the examples of the present disclosure more clearly, the drawings of the examples will be briefly introduced below. Apparently, the drawings in the following description only relate to some examples of the present disclosure, rather than limiting the present disclosure.

DETAILED DESCRIPTION OF THE EMBODIMENTS

Figure 1:
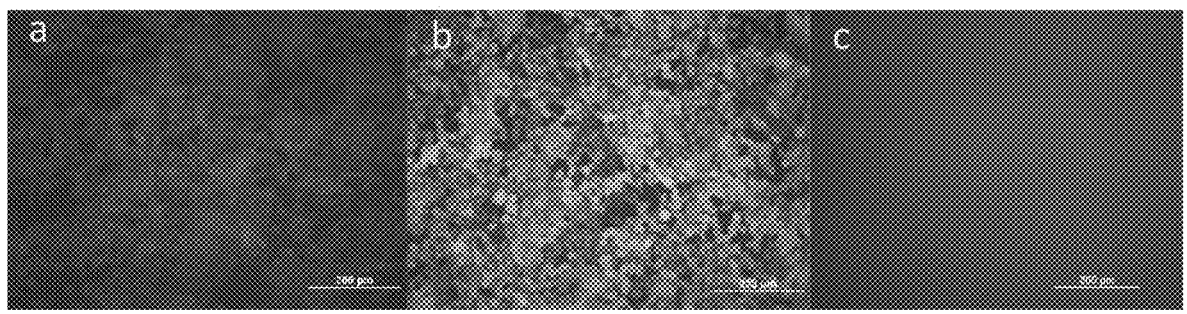
FIG. 1 shows the results of cell transfection tests with different weight ratios of the carrier (including YK-009) to mRNA used in the preparation of LNP formulations, wherein a has carrier:mRNA of 4:1, b has carrier:mRNA of 16:1, and c is a blank control.

In order to make the purpose, technical solutions and advantages of the examples of the present disclosure clearer, the technical solutions of the examples of the present disclosure will be clearly and completely described below in conjunction with the drawings of the examples of the present disclosure. Apparently, the described examples are some of the examples of the present disclosure, not all of them. Based on the described examples of the present disclosure, all other examples obtained by persons of ordinary skill in the art without creative efforts shall fall within the protection scope of the present disclosure.

The present disclosure may be embodied in other specific forms without departing from essential attributes of the present disclosure. It should be understood that any and all embodiments of the present disclosure can be combined with technical features in any other embodiment(s) to obtain additional embodiments under the premise of no conflict. The present disclosure includes additional embodiments obtained from such combinations.

All publications and patents mentioned in this disclosure are incorporated herein by reference in their entirety. If usage or terminology used in any publications and patents incorporated by reference conflicts with usage or terminology used in the present disclosure, the usage and terminology in the present disclosure shall control.

The section headings used herein are for the purpose of organizing the article only and should not be construed as limitations on the subject matter described.

Unless defined otherwise, all technical and scientific terms used herein have their ordinary meanings in the art to which the claimed subject matter belongs. In the event that more than one definitions exist for a term, the definition herein controls.

Except in the working examples or where otherwise indicated, all numbers stating quantitative properties such as dosages in the specification and claims are to be understood as modified in all instances by the term "about". It is also to be understood that any numerical range recited herein is intended to include all sub-ranges within that range and any combination of various endpoints of such ranges or sub-ranges.

The words "comprising", "including" or "containing" and similar words used in the present disclosure mean that the element appearing before the word covers the elements listed after the word and their equivalents, and does not exclude unrecited elements. The terms "comprising" or "including (containing)" used herein can be open, semi-closed and closed. In other words, the terms also include "consisting essentially of", or "consisting of".

The term "pharmaceutically acceptable" in this application means that a compound or composition is chemically and/or toxicologically compatible with the other ingredients making up the formulation and/or with the human or mammal in which it is used to prevent or treat a disease or condition.

The term "subject" or "patient" in this application includes humans and mammals.

The term "treating" as used herein refers to the administration of one or more drug substances to a patient or subject suffering from a disease or symptoms of the disease in order to cure, alleviate, relieve, ameliorate or affect the disease or symptoms of the disease. In the context of this application, unless specifically stated to the contrary, the term "treating" may also include prophylaxis.

The term "solvate" in this application refers to a complex formed by combining a compound of formula (I) or a pharmaceutically acceptable salt thereof with a solvent (e.g., ethanol or water). It should be understood that any solvate of a compound of formula I for use in the treatment of a disease or condition may provide different properties including pharmacokinetic properties, however will result in the compound of formula I upon absorption into a subject, such that the use of the compound of formula I encompasses the use of any solvate of the compound of formula I respectively.

The term "hydrate" refers to the situation where the solvent in the above term "solvate" is water.

It should be further understood that a compound of formula I, or a pharmaceutically acceptable salt thereof may be isolated in the form of a solvate, and therefore any such solvate is included within the scope of the present disclosure. For example, a compound of formula I, or a pharmaceutically acceptable salt thereof may exist in an unsolvated form as well as a solvated form with a pharmaceutically acceptable solvent such as water, ethanol, or the like.

The term "pharmaceutically acceptable salt" refers to a relatively non-toxic, inorganic or organic acid addition salt of a compound of the present disclosure. For example, see S. M. Berge et al. "Pharmaceutical Salts", *J. Pharm. Sci.* 1977, 66, 1-19. The inorganic acid is for example hydrochloric, hydrobromic, hydroiodic, sulfuric, phosphoric, or nitric acid; and the organic acid is for example formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, or sulfosalicylic acid. For example, a pharmaceutically acceptable salt may be formed by using a compound of formula I and HCl (or hydrochloric acid), HBr (or hydrobromic acid), methanesulfonic acid, sulfuric acid, tartaric acid or fumaric acid.

The nitrogen-containing compounds of formula (I) of the present disclosure may be converted to N-oxides by treatment with an oxidizing agent (e.g., m-chloroperbenzoic acid, hydrogen peroxide, ozone). Therefore, under the conditions allowed by the valence state and structure, the compounds claimed in this application include not only the nitrogen-containing compounds shown in the structural formulas, but also their N-oxide derivatives.

Certain compounds of the present disclosure may exist as one or more stereoisomers. Stereoisomers include geometric isomers, diastereomers and enantiomers. Accordingly, the compounds claimed in this disclosure also include racemic mixtures, single stereoisomers, and optically active mixtures. It will be understood by those skilled in the art that one stereoisomer may have better efficacy and/or lower side effects than other stereoisomers. Single stereoisomers and optically active mixtures can be obtained by methods such as chiral source synthesis, chiral catalysis, and chiral resolution. The racemate can be chirally resolved by chromatographic resolution or chemical resolution. For example, chiral tartaric acid, chiral malic acid or other chiral acid resolution reagents may be added to form a salt with the compound of the present disclosure, and the product may be separated by utilizing the different physical and chemical properties of the product, such as solubility.

The present disclosure also includes all suitable isotopic variations of the disclosed compounds. An isotopic variant is defined as a compound in which at least one atom is replaced by an atom of the same atomic number but with an atomic mass different from that commonly found or predominantly found in nature. Examples of isotopes that may be incorporated into compounds of the present disclosure include isotopes of hydrogen, carbon, nitrogen, and oxygen, such as $^2H$ (deuterium), $^3H$ (tritium), $^{11}C$, $^{13}C$, $^{14}C$, $^{15}N$, $^{17}O$, and $^{18}O$, respectively.

The term "alkyl" is used in this disclosure to include branched and linear saturated aliphatic monovalent hydrocarbon groups having the specified number of carbon atoms. The term "alkylene" is used in this disclosure to include branched and linear saturated aliphatic divalent hydrocarbon groups having the specified number of carbon atoms. $C_{n-m}$ refers to groups having n to m carbon atoms. For example, $C_{2-5}$ alkylene includes $C_2$ alkylene, $C_3$ alkylene, $C_4$ alkylene, and $C_5$ alkylene.

An alkyl (or alkylene) group can be unsubstituted, or an alkyl (or alkylene) group can be substituted wherein at least one hydrogen is replaced by another chemical group.

A "therapeutically effective amount" is an amount of a therapeutic agent being administered which will improve a disease or condition in a patient. A "prophylactically effective amount" is an amount of a prophylactic agent being administered which will prevent a disease or condition in a subject. The "therapeutically effective amount" for a therapeutic agent or the "prophylactically effective amount" for a prophylactic agent may vary with the therapeutic/prophylactic agent, the disease state and its severity, the age and weight of a patient/subject to be treated/prevented, etc. The therapeutically effective amount and the prophylactically effective amount can be routinely determined by one of ordinary skill in the art based on his knowledge and this disclosure.

In this application, when the name of the compound is inconsistent with the structural formula, the structural formula shall prevail.

It should be understood that the term "compound of the present disclosure" used in the present application may include the compound of formula I, N-oxide thereof, solvate thereof, pharmaceutically acceptable salt thereof, stereoisomer thereof, or mixture thereof according to the context.

The term "cationic lipid" as used herein refers to a lipid that is positively charged at a selected pH value.

Cationic lipids are prone to bind to negatively charged nucleic acids, that is, to form lipid nanoparticles (LNPs) by interacting with negatively charged phosphate groups present in nucleic acids through electrostatic forces. LNP is one of the mainstream delivery carriers at present.

After screening a large number of compounds, the inventors found that it is very difficult to screen out suitable cationic lipid compounds that meet the following conditions: high transfection efficiency and low cytotoxicity, as well as high and sustained expression in mice. The inventors have found that some compounds such as YK-009, YK-003, YK-006, YK-008 and YK-011 can deliver nucleic acids with high intracellular transfection efficiency, low or no cytotoxicity, and high and sustained expression in animals compared with the compounds in the prior art. Compounds with small structural differences may have very large differences in transfection efficiency and/or cytotoxicity and high expression in cells. For example, compounds YK-009 and YK-010 of the present application have nearly 60 times difference in cell transfection efficiency, and 25% or more of difference in toxicity to transfected cells. For another example, the difference in the expression and sustained expression of compounds YK-003 and YK-010 in mice can be 50 times.

Here, the cationic lipid DLin-MC3-DMA (MC3) disclosed by Alnylam Pharmaceuticals, Inc. (NASDAQ: ALNY) in CN102625696B is selected for comparison with our designed compounds. In addition to the efficient and safe delivery of siRNA, DLin-MC3-DMA (MC3) is now also widely used for mRNA delivery.

DLin-MC3-DMA (MC3) cationic lipid structure:

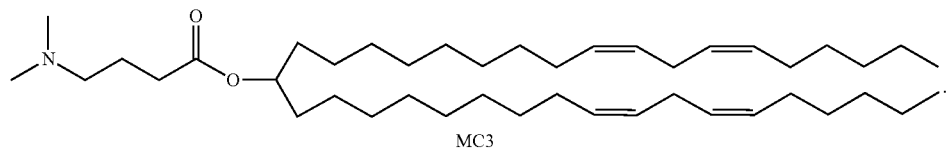 [SMILES: CCCCC/C=C\C/C=C\CCCCCCCCC(CCCCCCCC/C=C\C/C=C\CCCCC)OC(=O)CCCN(C)C]

MC3

In addition, the compounds of the present disclosure are also compared with the structurally similar compounds 23, 25 (namely, SM-102, CAS No.: 2089251-47-6, a cationic lipid used in Moderna's covid 19 vaccine mRNA-1273), and 27 in the patent CN110520409A filed by the Moderna company.

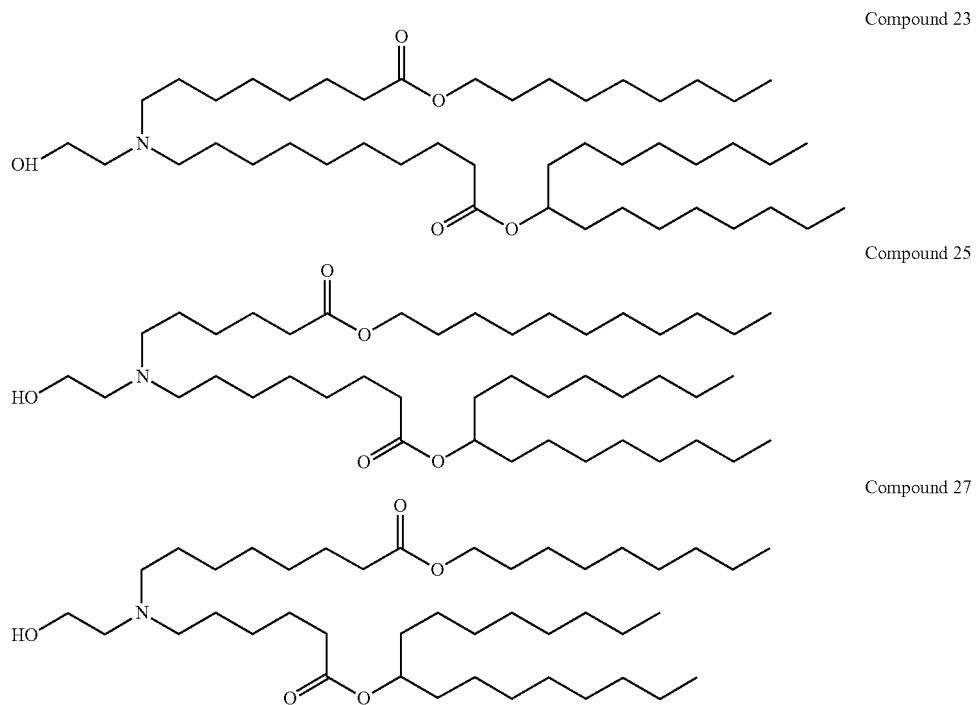

Compound 23

Compound 25

Compound 27

We found that the compounds of the present disclosure have significantly improved transfection efficiency and/or cytotoxicity. For example, regarding mRNA transfection, the cell transfection efficiency of compound YK-009 is 40 times, 8 times and 13 times higher than that of MC3, compound 23 and compound 27 respectively; the toxicity to transfected cells of compound YK-009 is 12%, 13% and 16% lower than that of MC3, compound 23 and compound 27 respectively; expression in mice for compound YK-009 is more than 25 times, 7 times and 6 times higher than that for MC3, compound 23 and compound 27, respectively; and expression in mice for compound YK-003 is more than 18 times, 8 times and 7 times higher than that for MC3, compound 23 and compound 27, respectively.

When mRNA is transfected, the compound YK-009 of the present disclosure has a 7-fold increase in cell transfection efficiency, a 9% reduction in toxicity to transfected cells, and a 7-fold increase in expression in mice compared with compound 25.

One aspect of the present disclosure provides novel cationic lipid compounds for the delivery of a therapeutic or prophylactic agent. The cationic lipid compounds of the present disclosure can be used to deliver nucleic acid molecules, small molecule compounds, polypeptides or proteins. Compared with known cationic lipid compounds, the cationic lipid compounds of the present disclosure exhibit higher transfection efficiency and less cytotoxicity, and thus improve delivery efficiency and safety.

The present disclosure provides a cationic lipid, which is a compound of formula (I)

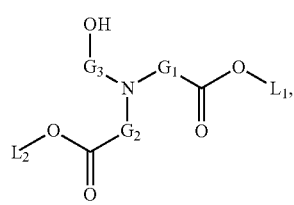

I or an N-oxide, solvate, pharmaceutically acceptable salt or stereoisomer thereof, wherein $G_1$ is $C_{1-6}$ alkylene, preferably unsubstituted $C_{2-5}$ alkylene, more preferably unsubstituted $C_3$ alkylene;

$G_2$ is $C_{2-8}$ alkylene, preferably unsubstituted $C_{4-6}$ alkylene, more preferably unsubstituted $C_5$ alkylene;

$G_3$ is $C_{1-3}$ alkylene, preferably unsubstituted $C_2$ alkylene;

$L_1$ is $C_{6-15}$ linear alkyl, preferably unsubstituted $C_{8-12}$ linear alkyl, more preferably unsubstituted $C_{10}$ linear alkyl;

$L_2$ is $C_{12-25}$ branched alkyl, preferably unsubstituted $C_{14-22}$ branched alkyl, more preferably unsubstituted $C_{18}$ branched alkyl.

In one embodiment, $G_1$ is unsubstituted $C_{2-5}$ alkylene, preferably unsubstituted $C_3$ alkylene, for example, —$(CH_2)_3$—.

In one embodiment, $G_2$ is unsubstituted $C_{4-6}$ alkylene, preferably unsubstituted $C_5$ alkylene, for example, —$(CH_2)_5$—.

In one embodiment, $G_3$ is unsubstituted $C_2$ alkylene, i.e., —$(CH_2)_2$—.

In one embodiment, $L_1$ is unsubstituted $C_{8-12}$ linear alkyl, preferably unsubstituted $C_{10}$ linear alkyl, for example, —$(CH_2)_9CH_3$.

In one embodiment, $L_2$ is unsubstituted $C_{14-22}$ branched alkyl, preferably unsubstituted $C_{18}$ branched alkyl. For example, $L_2$ is:

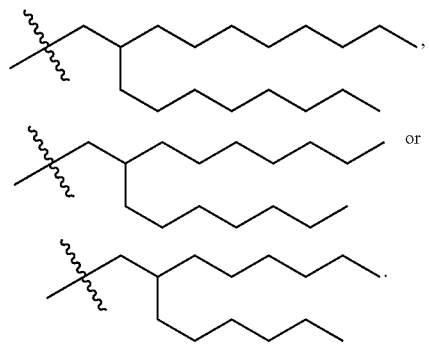

In one embodiment, $G_1$ is —$(CH_2)_3$—, $G_2$ is —$(CH_2)_5$—, $G_3$ is —$(CH_2)_2$—, $L_1$ is —$(CH_2)_9CH_3$, $L_2$ is:

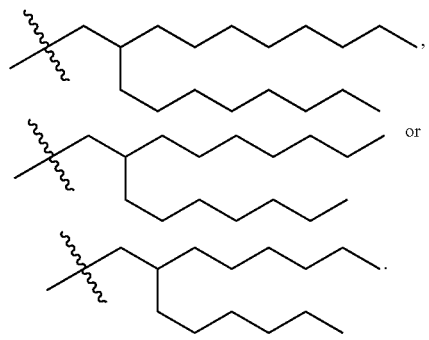

In an exemplary embodiment, the compound is selected from the following compounds or N-oxides, solvates, pharmaceutically acceptable salts or stereoisomers thereof:

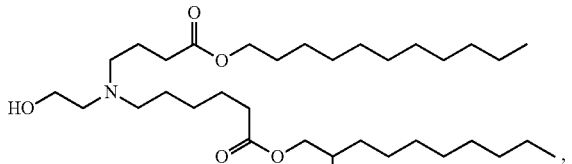
YK-001

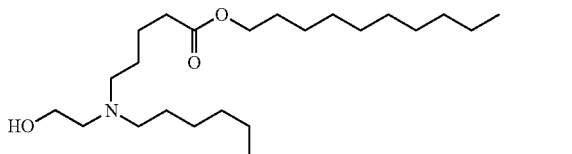
YK-002

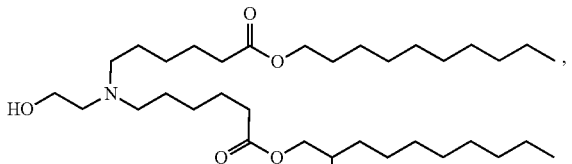
YK-003

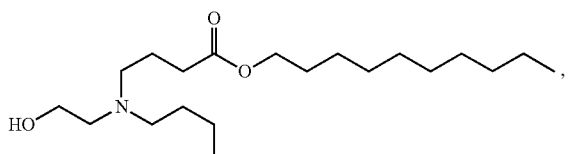
YK-004

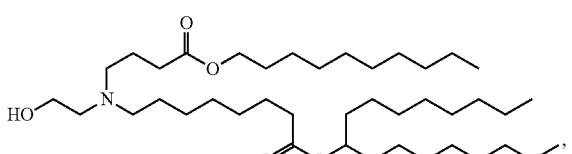
YK-005

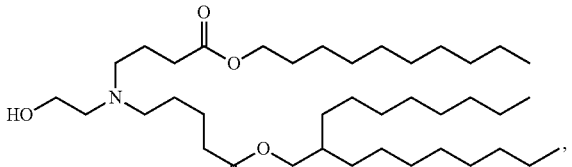
YK-006

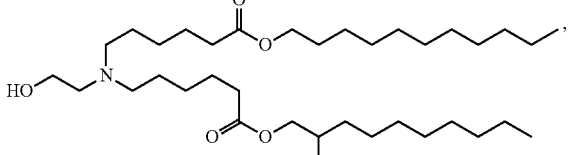
YK-007

-continued

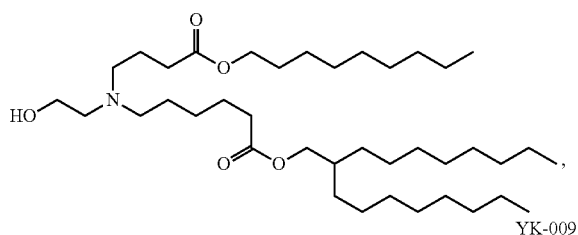
YK-008,

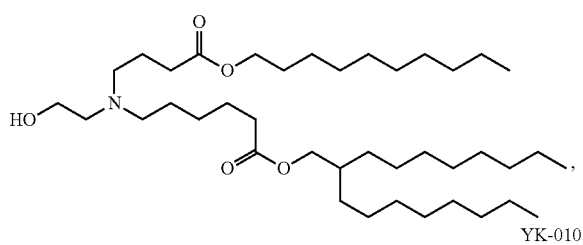
YK-009,

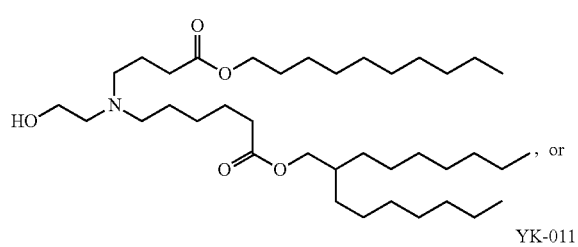
YK-010, or

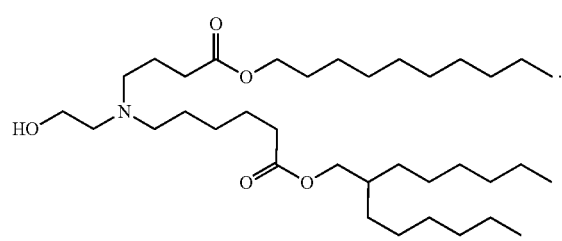
YK-011.

Another aspect of the present disclosure provides a composition comprising a carrier, wherein the carrier includes a cationic lipid, and the cationic lipid includes the above compound of formula (I) or an N-oxide, solvate, pharmaceutically acceptable salt or stereoisomer thereof.

In one embodiment, the composition is a nanoparticle formulation, wherein the average size of the nanoparticle formulation is 10 nm to 210 nm, preferably 100 nm to 205 nm; and the polydispersity coefficient of the nanoparticle formulation is ≤50%, preferably ≤ 30%, more preferably ≤25%.

Cationic Lipid

In one embodiment of the composition/carrier of the present disclosure, the cationic lipid is one or more selected from the above compound of formula (I) or an N-oxide, solvate, pharmaceutically acceptable salt or stereoisomer thereof. In one embodiment, the cationic lipid is selected from the compounds of formula (I) described above. For example, the cationic lipid is compound YK-001, YK-002, YK-003, YK-004, YK-005, YK-006, YK-007, YK-008, YK-009, YK-010 or YK-011. In a preferred embodiment, the cationic lipid is compound YK-009.

In another embodiment of the composition/carrier of the present disclosure, the cationic lipid comprises: (a) one or more selected from the above compound of formula (I) or an N-oxide, solvate, pharmaceutically acceptable salt or stereoisomer thereof; and (b) one or more other ionizable lipid compound(s) different from (a). The cationic lipid compound (b) can be a commercially available cationic lipid, or a cationic lipid compound reported in literatures. For example, the cationic lipid compound (b) can be DLin-MC3-DMA (MC3). For another example, the cationic lipid compound (b) can be compound 23, 25, or 27, etc. in CN110520409A.

In one embodiment, the molar ratio of the cationic lipid to the carrier is 30% to 70%, such as 35%, 45%, 50%, 55%, 60%, or 65%.

The carrier can be used to deliver an active ingredient such as a therapeutic or prophylactic agent. The active ingredient can be sealed within the carrier or bound to the carrier.

For example, the therapeutic or prophylactic agent includes one or more of nucleic acid molecules, small molecule compounds, polypeptides or proteins. Such nucleic acids include, but are not limited to, single-stranded DNA, double-stranded DNA, and RNA. Suitable RNAs include, but are not limited to, small interfering RNA (siRNA), asymmetric interfering RNA (aiRNA), microRNA (miRNA), Dicer-substrate RNA (dsRNA), small hairpin RNA (shRNA), messenger RNA (mRNA) and mixtures thereof.

Neutral Lipid

The carrier may comprise a neutral lipid. Neutral lipid in this disclosure refers to an auxiliary lipid that is uncharged or exists in a zwitterionic form at a selected pH value. The neutral lipid may regulate the flow of nanoparticles into a lipid bilayer structure and improve efficiency by promoting lipid phase transition, while also possibly affecting target organ specificity.

In one embodiment, the molar ratio of the cationic lipid to the neutral lipid is about 1:1 to 10:1, for example about 9:1, 8:1, 7:1, 6:1, 5:1, 4:1, or 3:1. In a preferred embodiment, the molar ratio of the cationic lipid to the neutral lipid is about 5:1.

For example, neutral lipids may include one or more of phosphatidylcholine, phosphatidylethanolamine, sphingomyelin, ceramide, sterol, and derivatives thereof.

The carrier component of a composition comprising the cationic lipid may comprise one or more neutral lipid-phospholipids, such as one or more (poly) unsaturated lipids. Phospholipids can be assembled into one or more lipid bilayers. In general, a phospholipid can comprise a phospholipid moiety and one or more fatty acid moieties.

The neutral lipid moiety may be selected from the non-limiting group consisting of phosphatidylcholine, phosphatidylethanolamine, phosphatidylglycerol, phosphatidylserine, phosphatidic acid, 2-lysophosphatidylcholine, and sphingomyelin. The fatty acid moiety may be selected from the non-limiting group consisting of lauric acid, myristic acid, myristoleic acid, palmitic acid, palmitoleic acid, stearic acid, oleic acid, linoleic acid, alpha-linolenic acid, erucic acid, phytanic acid, arachidic acid, arachidonic acid, eicosapentaenoic acid, behenic acid, docosapentaenoic acid, and docosahexaenoic acid. Also contemplated are non-natural species which include natural species with modifications and substitutions such as branching, oxidation, cyclization and alkynes. For example, a phospholipid can be functionalized with or cross-linked with one or more alkynes (e.g., an alkenyl group in which one or more double bonds are replaced by a triple bond). Under appropriate reaction conditions, alkynyl groups may undergo copper-catalyzed cycloaddition reactions when exposed to azides. These reactions can be used to functionalize the lipid bilayer of the composition to facilitate membrane penetration or cell recognition, or to couple the composition to useful components such as targeting or imaging moieties (e.g., dyes).

Neutral lipids useful in these compositions can be selected from the non-limiting group consisting of: 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), PC), 1-hexadecyl-sn-glycero-3-phosphocholine (C16 Lyso 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoyl phosphatidylglycerol (DPPG), palmitoyl oleoyl phosphatidylethanolamine (POPE), distearoyl-phosphatidyl-ethanolamine (DSPE), dipalmitoyl phosphatidylethanolamine (DPPE), dimyristoyl phosphoethanolamine (DMPE), 1-stearyl-2-oleoyl-stearoylethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyl oleoyl phosphatidylcholine, lysophosphatidylcholine, lysophosphatidylethanolamine (LPE), and mixtures thereof.

In some embodiments, the neutral lipid comprises DSPC. In certain embodiments, the neutral lipid comprises DOPE. In some embodiments, the neutral lipid comprises both DSPC and DOPE.

Structured Lipid

The carrier of the composition including the cationic lipid may also include one or more structured lipid(s). Structured lipids in this disclosure refer to lipids that enhance the stability of nanoparticles by filling the gaps between lipids.

In one embodiment, the molar ratio of the cationic lipid to the structured lipid is about 1:1 to 5:1, for example, about 1.0:1, 1.1:1, 1.2:1, 1.3:1, 1.4:1, 1.5:1, 1.6:1, 1.7:1, 1.8:1, 1.9:1, or 2.0:1.

Structured lipids may be selected from, but are not limited to, the group consisting of cholesterol, nonsterol, sitosterol, ergosterol, campesterol, stigmasterol, brassicasterol, tomatine, tomatine, ursolic acid, alpha-tocopherol, corticosteroid and mixtures thereof. In some embodiments, the structured lipid is cholesterol. In some embodiments, the structured lipid includes cholesterol, corticosteroid (e.g., prednisolone, dexamethasone, prednisone, and hydrocortisone) or a combination thereof.

Polymer-Conjugated Lipid

The carrier of the composition including the cationic lipid may also include one or more polymer-conjugated lipid(s). Polymer-conjugated lipids mainly refer to lipids modified with polyethylene glycol (PEG). Hydrophilic PEG stabilizes LNPs, regulates nanoparticle size by limiting lipid fusion, and increases nanoparticle half-life by reducing nonspecific interactions with macrophages.

In one embodiment, the polymer-conjugated lipid is selected from one or more of PEG-modified phosphatidylethanolamine, PEG-modified phosphatidic acid, PEG-modified ceramide, PEG-modified dialkylamine, PEG-modified diacylglycerol, and PEG-modified dialkylglycerol. The molecular weight of PEG for the PEG modification is usually 350-5000 Da.

For example, the polymer-conjugated lipid is selected from one or more of distearoyl phosphatidylethanolamine polyethylene glycol 2000 (DSPE-PEG2000), dimyristoylglycero-3-methoxy polyethylene glycol 2000 (DMG-PEG2000) and methoxypolyethylene glycol ditetradecylacetamide (ALC-0159).

In one embodiment of the composition/carrier of the present disclosure, the polymer-conjugated lipid is DMG-PEG2000.

In one embodiment of the composition/carrier of the present disclosure, the carrier includes a neutral lipid, a structured lipid and a polymer-conjugated lipid, wherein the molar ratio of the cationic lipid, the neutral lipid, the structured lipid, and the polymer-conjugated lipids is (25-65):(5-25):(25-45):(0.5-5), for example (45-55):(9-11):(34~43):(0.5~2.5).

In one embodiment of the composition/carrier of the present disclosure, the carrier includes a neutral lipid, a structured lipid and a polymer-conjugated lipid, wherein the molar ratio of the cationic lipid, the neutral lipid, the structured lipid, and the polymer-conjugated lipid is 50:10:38.5:1.5.

Therapeutic and/or Prophylactic Agent

The composition may include one or more therapeutic and/or prophylactic agent(s). In one embodiment, the mass ratio of the carrier to the therapeutic or prophylactic agent is from 10:1 to 30:1, for example 15:1, 16:1, 17:1, 18:1, 19:1, 20:1, 21:1, 22:1, 23:1, 24:1, or 25:1.

In one embodiment, the mass ratio of the carrier to the therapeutic or prophylactic agent is from 15:1 to 25:1, preferably 16:1.

The therapeutic or prophylactic agent includes, but is not limited to, one or more of a nucleic acid molecule, a small molecule compound, a polypeptide or a protein.

For example, the therapeutic or prophylactic agent is a vaccine or compound capable of eliciting an immune response.

The carriers of the present disclosure can deliver therapeutic and/or prophylactic agents to mammalian cells or organs, and thus the present disclosure also provides methods of treating diseases or conditions in mammals in need thereof, which include administering to the mammal a composition comprising a therapeutic and/or prophylactic agent and/or contacting mammalian cells with the composition.

Therapeutic and/or prophylactic agents include biologically active substances and are referred to alternatively as "active agents." A therapeutic and/or prophylactic agent may be a substance that, after delivery to a cell or organ, causes a desired change in the cell or organ or in other tissues or systems of the body. Such species can be used to treat one or more diseases, disorders or conditions. In some embodiments, the therapeutic and/or prophylactic agent is a small molecule drug useful in the treatment of a particular disease, disorder or condition. Examples of drugs that can be used in the composition include, but are not limited to, antineoplastic agents (e.g., vincristine, doxorubicin, mitoxantrone, camptothecin, cisplatin, bleomycin, cyclophosphamide, methotrexate, and streptozotocin), antitumor agents (e.g., actinomycin D, vincristine, vinblastine, cytosine arabinoside, anthracycline, alkylating agents, platinum compounds, antimetabolites, and nucleoside analogs such as methotrexate and purine and pyrimidine analogs), anti-infectives, local anesthetics (e.g., dibucaine and chlorpromazine), beta-adrenergic blockers (e.g., propranolol, timolol and labetalol), antihypertensives (e.g., clonidine and hydralazine), antidepressants (e.g., imipramine, amitriptyline, and doxepin), anticonvulsants (e.g., phenytoin), antihistamines (e.g., diphenhydramine, chlorpheniramine, and promethazine), antibiotics/antibacterials (e.g., gentamycin, ciprofloxacin, and cefoxitin), antifungals (e.g., miconazole, terconazole, econazole, isoconazole, butaconazole, clotrimazole, itraconazole, nystatin, naftifine, and amphotericin B), antiparasitic agents, hormones, hormone antagonists, immunomodulators, neurotransmitter antagonists, antiglaucoma drugs, vitamins, sedatives, and imaging agents.

In some embodiments, the therapeutic and/or prophylactic agent is a cytotoxin, a radioactive ion, a chemotherapeutic agent, a vaccine, a compound that elicits an immune response, and/or another therapeutic agent and/or prophylactic agent. A cytotoxin or cytotoxic agent includes any agent that is harmful to cells. Examples include, but are not limited to, taxol, cytochalasin B, gramicidin D, ethidium bromide, emetine, mitomycin, etoposide, teniposide, vincristine, vinblastine, colchicine, doxorubicin, daunorubicin, dihydroxy anthracin dione, mitoxantrone, mithramycin, actinomycin D, 1-dehydrotestosterone, glucocorticoid, procaine, tetracaine, lidocaine, propranolol, puromycin, maytansinoids such as maytansinol, rachelmycin (CC-1065), and their analogs or homologues. Radioactive ions include, but are not limited to, iodine (e.g., iodine 125 or iodine 131), strontium 89, phosphorus, palladium, cesium, iridium, phosphate, cobalt, yttrium 90, samarium 153, and praseodymium. Vaccines include compounds and formulations that confer immunity against one or more conditions associated with infectious diseases such as influenza, measles, human papillomavirus (HPV), rabies, meningitis, pertussis, tetanus, plague, hepatitis and tuberculosis, and may include mRNA encoding infectious disease-derived antigens and/or epitopes. Vaccines may also include compounds and formulations that lead to an immune response against cancer cells and may include mRNA encoding tumor cell-derived antigens, epitopes and/or neo-epitopes. Compounds that elicit an immune response may include vaccines, corticosteroids (e.g., dexamethasone), and other species. In some embodiments, vaccines and/or compounds capable of eliciting an immune response are administered by intramuscular administration of a composition comprising a compound according to formula (I), (IA), (IB), (II), (IIa), (IIb), (IIc), (IId), (IIe), (IIf), (IIg) or (III) (e.g., compound 3, 18, 20, 25, 26, 29, 30, 60, 108-112 or 122). Other therapeutic and/or prophylactic agents include, but are not limited to, antimetabolites (e.g., methotrexate, 6-mercaptopurine, 6-thioguanine, cytarabine, 5-fluorouracil, and dacarbazine), alkanes (e.g., mechlorethamine, thiotepa, chlorambucil, lazithromycin (CC-1065), melphalan, carmustine (BSNU), lomustine (CCNU), cyclophosphamide, busulfan, dibromomannitol, streptozotocin, mitomycin C, and cis-dichlorodiamino platinum (II) (DDP), cisplatin), anthracyclines (e.g., daunorubicin (formerly known as daunomycin) and doxorubicin), antibiotics (e.g., dactinomycin (formerly known as actinomycin), bleomycin, mithramycin, and anthramycin (AMC)) and antimitotic agents (e.g., vincristine, vinblastine, paclitaxel, and maytansinoid).

In other embodiments, the therapeutic and/or prophylactic agent is a protein. Therapeutic proteins that can be used in the nanoparticles of the present disclosure include, but are not limited to, gentamicin, amikacin, insulin, erythropoietin (EPO), granulocyte colony stimulating factor (G-CSF), granulocyte-macrophage colony-stimulating factor (GM-CSF), factor VIR, luteinizing hormone-releasing hormone (LHRH) analogs, interferon, heparin, hepatitis B surface antigen, typhoid vaccines and cholera vaccines.

In some embodiments, the therapeutic agent is a polynucleotide or nucleic acid (e.g., ribonucleic acid or deoxyribonucleic acid). The term "polynucleotide" in its broadest sense includes any compound and/or substance which is an oligonucleotide chain or can be incorporated into an oligonucleotide chain. Exemplary polynucleotides for use in accordance with the present disclosure include, but are not limited to, one or more of deoxyribonucleic acid (DNA); ribonucleic acid (RNA), including messenger mRNA (mRNA), hybrids thereof; RNAi-inducing factors; RNAi factors; siRNA; shRNA; miRNA; antisense RNA; ribozyme; catalytic DNA; RNA that induces triple helix formation; aptamer, etc. In some embodiments, the therapeutic and/or prophylactic agent is RNA. RNAs useful in the compositions and methods described herein can be selected from the group consisting of, but not limited to, shortmer, antagomir, antisense RNA, ribozymes, small interfering RNA (siRNA), asymmetric interfering RNA (aiRNA), microRNA (miRNA), Dicer-substrate RNA (dsRNA), small hairpin RNA (shRNA), transfer RNA (tRNA), messenger RNA (mRNA) and mixtures thereof. In certain embodiments, the RNA is mRNA.

In certain embodiments, the therapeutic and/or prophylactic agent is mRNA. The mRNA can encode any polypeptide of interest, including any naturally or non-naturally occurring or otherwise modified polypeptide. The polypeptide encoded by the mRNA can be of any size and can have any secondary structure or activity. In some embodiments, the polypeptide encoded by an mRNA may have a therapeutic effect when expressed in a cell.

In other embodiments, the therapeutic and/or prophylactic agent is siRNA. The siRNA can selectively reduce the expression of a gene of interest or downregulate the expression of that gene. For example, the siRNA can be selected such that a gene associated with a particular disease, disorder or condition is silenced upon administration of a composition comprising the siRNA to a subject in need thereof. siRNA can comprise a sequence that is complementary to an mRNA sequence encoding a gene or protein of interest. In some embodiments, the siRNA can be an immunomodulatory siRNA.

In certain embodiments, the therapeutic and/or prophylactic agent is sgRNA and/or cas9 mRNA. sgRNA and/or cas9 mRNA can be used as gene editing tools. For example, sgRNA-cas9 complexes can affect mRNA translation of cellular genes.

In some embodiments, the therapeutic and/or prophylactic agent is shRNA or a vector or plasmid encoding shRNA. shRNA can be produced inside a target cell after an appropriate construct is delivered into the nucleus. The constructs and mechanisms associated with shRNA are well known in the related art.

Disease or Condition

The composition/carrier of the present disclosure can deliver a therapeutic or prophylactic agent to a subject or patient. The therapeutic or prophylactic agent includes, but is not limited to, one or more of nucleic acid molecules, small molecular compounds, polypeptides or proteins. Therefore, the composition of the present disclosure can be used to prepare nucleic acid medicine, gene vaccine, small molecule medicine, polypeptide or protein medicine. Due to the wide variety of therapeutic or prophylactic agents described above, the composition of the present disclosure can be used to treat or prevent a variety of diseases or conditions.

In one embodiment, the disease or condition is characterized by dysfunctional or abnormal protein or polypeptide activity.

For example, the disease or condition is selected from the group consisting of infectious diseases, cancer and proliferative diseases, genetic diseases, autoimmune diseases, diabetes, neurodegenerative diseases, cardiovascular and renovascular diseases, and metabolic diseases.

In one embodiment, the infectious disease is selected from diseases caused by coronavirus, influenza virus, or HIV virus, infantile pneumonia, Rift Valley fever, yellow fever, rabies, and various herpes.

Other Components

The composition may include one or more component(s) other than those described in the preceding sections. For example, the composition may include one or more small hydrophobic molecules, such as vitamins (e.g., vitamin A or vitamin E) or sterols.

The composition may also include one or more permeability enhancing molecules, carbohydrates, polymers, surface-altering agents or other components. The permeability enhancing molecule can be, for example, molecules described in US Patent Application Publication No. 2005/0222064. The carbohydrates can include simple sugars such as glucose and polysaccharides such as glycogen and derivatives and analogs thereof.

Surface-altering agents may include, but are not limited to, anionic proteins such as bovine serum albumin, surfactants for example cationic surfactants such as dimethyldioctadecylammonium bromide, sugars or sugar derivatives (e.g., cyclodextrins), nucleic acids, polymers (e.g., heparin, polyethylene glycol, and poloxamers), mucolytics (e.g., acetylcysteine, mugwort, bromelain, papain, clerodendrum, bromhexine, carbocisteine, eprazinone, mesna, ambroxol, sobrerol, domiodol, letosteine, stepronin, tiopronin, gelsolin, thymosin β4, dornase alfa, neltenexine and erdosteine) and DNases (e.g., rhDNase). Surface-altering agents can be disposed within and/or on the surface of the nanoparticles of the composition (e.g., by coating, adsorption, covalent attachment, or other methods).

The composition may also comprise one or more functionalized lipids. For example, lipids can be functionalized with alkyne groups that may undergo cycloaddition reactions when exposed to azide under appropriate reaction conditions. Specifically, lipid bilayers can be functionalized in this way with one or more groups that effectively facilitate membrane penetration, cell recognition, or imaging. The surface of the composition may also be coupled to one or more useful antibodies. Functional groups and conjugates useful for targeted cell delivery, imaging and membrane penetration are well known in the art.

In addition to these components, the composition may include any material that can be used in pharmaceutical compositions. For example, a composition may include one or more pharmaceutically acceptable excipients or auxiliary ingredients, such as, but not limited to, one or more of solvents, dispersion media, diluents, dispersion aids, suspension aids, granulation aids, disintegrants, fillers, glidants, liquid vehicles, binders, surfactants, isotonic agents, thickeners, emulsifiers, buffers, lubricants, oils, preservatives, flavoring agents, colorants, etc. Excipients are, for example, starch, lactose or dextrin. Pharmaceutically acceptable excipients are well known in the art (see for example Remington's The Science and Practice of Pharmacy, 21st Edition, A. R. Gennaro; Lippincott, Williams & Wilkins, Baltimore, M D, 2006).

Examples of diluents may include, but are not limited to, calcium carbonate, sodium carbonate, calcium phosphate, dicalcium phosphate, calcium sulfate, calcium hydrogen phosphate, sodium phosphate, lactose, sucrose, cellulose, microcrystalline cellulose, kaolin, mannitol, sorbitol, inositol, sodium chloride, dry starch, corn starch, powdered sugar and/or a combination thereof.

In some embodiments, compositions comprising one or more lipids described herein may also include one or more adjuvants, such as glucopyranosyl lipid adjuvant (GLA), CpG oligodeoxyribonucleotide (e.g., class A or class B), poly(I:C), aluminum hydroxide, and Pam3CSK4.

The compositions of the present disclosure can be formulated in solid, semi-solid, liquid or gaseous form, such as tablets, capsules, ointments, elixirs, syrups, solutions, emulsions, suspensions, injections, and aerosols. The compositions of the present disclosure can be prepared by methods well known in the art of pharmacy. For example, sterile injectable solutions can be prepared by incorporating into an appropriate solvent such as sterile distilled water the therapeutic or prophylactic agent in the required amount with various other ingredients enumerated above as required and then filtered sterilization. Surfactants may also be added to promote the formation of a uniform solution or suspension. For example, compositions of the present disclosure may be administered intravenously, intramuscularly, intradermally, subcutaneously, intranasally, or by inhalation. In one embodiment, the composition is administered subcutaneously.

The compositions of the present disclosure are administered in therapeutically effective amounts which may vary not only with the particular agent chosen, but also with the route of administration, the nature of the disease being treated, and the age and condition of the patient, and may ultimately be at the discretion of the attending physician or clinician. For example, a dose of about 0.001 mg/kg to about 10 mg/kg of the therapeutic or prophylactic agent can be administered to a mammal (e.g., a human).

EXAMPLE

The present disclosure will be further described below in conjunction with the examples, but the present disclosure is not limited to the following examples. Examples without specific conditions were carried out under conventional conditions or conditions suggested by the manufacturer. Reagents or instruments whose manufacturers were not indicated were all conventional products commercially available.

Example 1: Synthesis of Cationic Lipid Compounds

1. Synthesis of 6-((4-(undecyloxy)-4-oxobutyl)(2-hydroxyethyl)amino)hexanoate (YK-001)

The synthetic route is as follows:

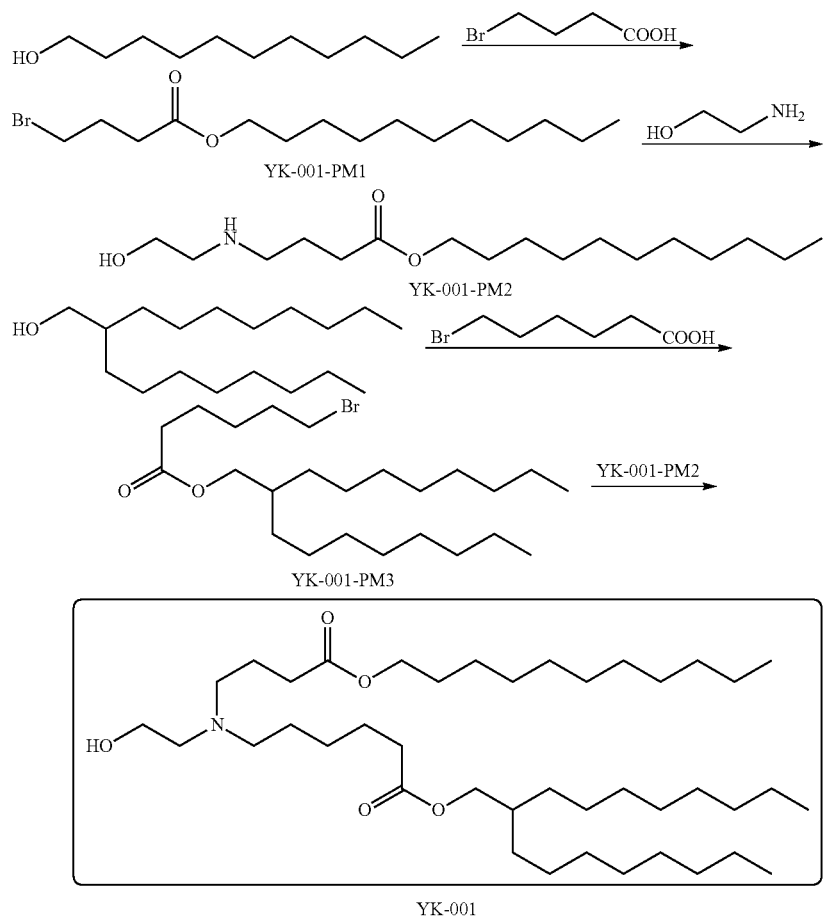

Step 1: Synthesis of n-undecyl 4-bromobutyrate (YK-001-PM1)

n-Undecyl alcohol (5.00 g, 29.02 mmol) and 4-bromobutanoic acid (5.14 g, 30.78 mmol) were dissolved in dichloromethane (40 mL). To the above solution were added 1-(3-dimethylaminopropyl)-3-ethylcarbodiimide hydrochloride (6.67 g, 34.82 mmol) and 4-dimethylaminopyridine (177 mg, 1.45 mmol). The mixture was stirred and reacted at 30~35° C. for 8 hours. After the reaction was completed, the reaction solution was washed successively with saturated sodium carbonate and saturated brine, and dried over $Na_2SO_4$. The mixture was filtered, and the filtrate was concentrated under reduced pressure in vacuo. The residue was purified by silica gel chromatography to give n-undecyl 4-bromobutyrate (6.68 g, 20.79 mmol, 71.64%).

$^1$H NMR (400 MHZ, $CDCl_3$) δ 4.08 (t, J=6.8 Hz, 2H), 3.47 (t, J=6.5 Hz, 2H), 2.50 (t, J=7.2 Hz, 2H), 2.18 (p, J=6.8 Hz, 2H), 1.61 (dd, J=14.2, 7.0 Hz, 2H), 1.39-1.19 (m, 16H), 0.88 (t, J=6.9 Hz, 3H).

Step 2: Synthesis of n-undecyl 4-((2-hydroxyethyl)amino)butyrate (YK-001-PM2)

n-Undecyl 4-bromobutyrate (2.71 g, 8.43 mmol) and ethanolamine (1.40 g, 22.92 mmol) were dissolved in acetonitrile (50 mL). To the above system was added potassium carbonate (3.17 g, 22.92 mmol). The mixture was heated to 70° C. and reacted with stirring for 2 hours. After the reaction was completed, the reaction solution was cooled to room temperature and filtered, and the filtrate was concentrated under reduced pressure in vacuo to remove the solvent. The residue was purified by silica gel chromatography to give n-undecyl 4-((2-hydroxyethyl)amino)butyrate (1.47 g, 4.88 mmol, 57.89%). $C_{17}H_{35}NO_3$, MS (ES): m/z (M+H$^+$) 302.2.

$^1$H NMR (400 MHZ, $CDCl_3$) δ 4.06 (t, J=6.8 Hz, 2H), 3.67-3.60 (m, 3H), 2.82-2.77 (m, 2H), 2.69 (t, J=7.0 Hz, 2H), 2.38 (t, J=7.3 Hz, 2H), 2.13-2.02 (m, 3H), 1.84 (p, J=7.2 Hz, 2H), 1.66-1.53 (m, 2H), 1.28 (d, J=15.5 Hz, 14H), 0.89 (d, J=6.7 Hz, 3H).

Step 3: Synthesis of 2-octyldecyl 6-bromohexanoate (YK-001-PM3)

According to the method for preparing YK-001-PM1, 6-bromohexanoic acid (2.60 g, 13.33 mmol) and 2-octyldecanol (3.00 g, 11.09 mmol) were used as raw materials to give 2-octyldecyl 6-bromohexanoate (3.05 g, 6.82 mmol, 61.50%).

$^1$H NMR (400 MHZ, CDCl$_3$) δ 3.97 (d, J=5.8 Hz, 2H), 3.40 (t, J=6.8 Hz, 2H), 2.33 (t, J=7.4 Hz, 2H), 1.93-1.84 (m, 2H), 1.66 (dt, J=20.5, 7.4 Hz, 3H), 1.48 (m, J=8.6, 6.9, 4.2 Hz, 2H), 1.35-1.19 (m, 28H), 0.88 (t, J=6.9 Hz, 6H).

Step 4: Synthesis of 2-octyldecyl 6-((4-(undecyloxy)-4-oxobutyl) (2-hydroxyethyl)amino)hexanoate (YK-001)

2-Octyldecyl 6-bromohexanoate (200 mg, 0.45 mmol) and n-undecyl 4-((2-hydroxyethyl)amino)butyrate (102 mg, 0.34 mmol) were dissolved in acetonitrile (10 mL). To the above system were added potassium carbonate (188 mg, 1.36 mmol) and potassium iodide (5 mg, 0.03 mmol). The mixture was heated to 70° C. and reacted with stirring for 20 hours. The reaction solution was cooled to room temperature and filtered, and the filtrate was concentrated in vacuo to remove the solvent. The residue was purified by silica gel chromatography to give the title compound (36 mg, 0.054 mmol, 14.7%). C$_{41}$H$_{81}$NO$_5$, MS (ES): m/z (M+H$^+$) 668.6.

$^1$H NMR (400 MHZ, CDCl$_3$) δ 4.06 (t, J=6.8 Hz, 2H), 3.97 (d, J=5.8 Hz, 2H), 3.84-3.72 (m, 1H), 3.53-3.48 (m, 1H), 3.46-3.40 (m, 1H), 2.42 (d, J=8.3 Hz, 1H), 2.32 (dd, J=15.2, 7.6 Hz, 4H), 2.13-2.04 (m, 1H), 1.70-1.57 (m, 6H), 1.39-1.18 (m, 53H), 0.88 (t, J=6.8 Hz, 9H).

2. Synthesis of 6-((5-(decyloxy)-5-oxopentyl)(2-hydroxyethyl)amino)hexanoate (YK-002) 2-octyldecyl The synthetic route is as follows:

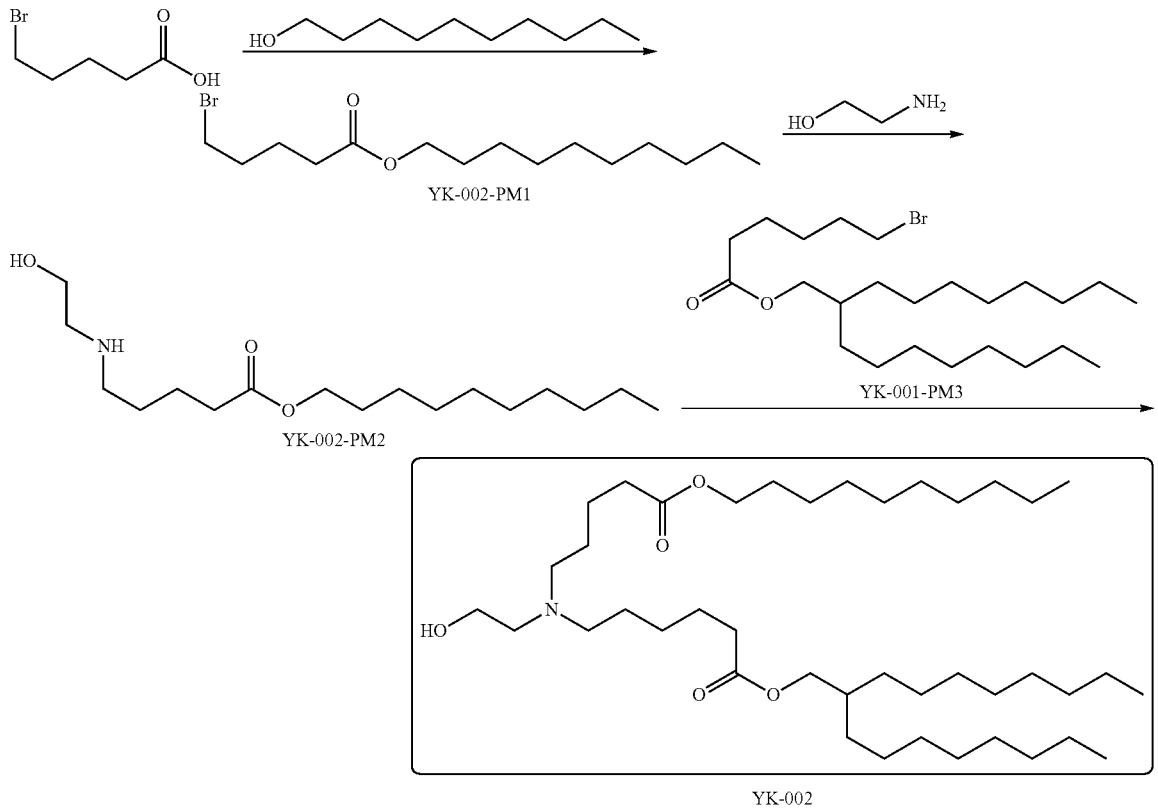

Step 1: Synthesis of n-decyl 5-bromopentanoate (YK-002-PM1)

According to the method for preparing YK-001-PM1, 5-bromopentanoic acid (1.81 g, 10.00 mmol) and n-decanol (1.45 g, 9.16 mmol) were used as raw materials to give n-decyl 5-bromopentanoate (2.50 g, 7.78 mmol, 84.93%).

$^1$H NMR (400 MHZ, CDCl$_3$) δ 4.07 (t, J=6.8 Hz, 2H), 3.41 (t, J=6.6 Hz, 2H), 2.34 (t, J=7.3 Hz, 2H), 1.96-1.85 (m, 2H), 1.83-1.73 (m, 2H), 1.69-1.54 (m, 2H), 1.31 (dd, J=18.9, 15.6 Hz, 14H), 0.88 (t, J=6.9 Hz, 3H).

Step 2: Synthesis of n-decyl 5-((2-hydroxyethyl)amino)pentanoate (YK-002-PM2)

According to the method for preparing YK-001-PM2, n-decyl 5-bromopentanoate (1.92 g, 5.98 mmol) and ethanolamine (0.31 g, 5.07 mmol) were used as raw materials to give n-decyl 5-((2-hydroxyethyl)amino)pentanoate (0.34 g, 1.13 mmol, 18.90%). C$_{17}$H$_{35}$NO$_3$, MS (ES): m/z (M+H$^+$) 302.3.

$^1$H NMR (400 MHZ, CDCl$_3$) δ 4.05 (dd, J=8.9, 4.7 Hz, 1H), 4.00-3.92 (m, 1H), 3.82-3.77 (m, 2H), 3.63 (t, J=6.7 Hz, 2H), 3.58-3.51 (m, 2H), 3.37 (t, J=5.3 Hz, 2H), 2.41 (m,

2H), 1.84-1.76 (m, 4H), 1.66-1.51 (m, 4H), 1.28 (d, J=14.2 Hz, 12H), 0.88 (t, J=6.8 Hz, 3H).

Step 3: Synthesis of 2-octyldecyl 6-((5-(decyloxy)-5-oxopentyl)(2-hydroxyethyl)amino)hexanoate (YK-002)

According to the method for preparing YK-001, n-decyl 5-((2-hydroxyethyl)amino)pentanoate (151 mg, 0.50 mmol) and 2-octyldecyl 6-bromohexanoate (226 mg, 0.50 mmol) were used as raw materials to give the target compound (216 mg, 0.32 mmol, 64.0%). $C_{41}H_{81}NO_5$, MS (ES): m/z (M+H$^+$) 668.5.

$^1$H NMR (400 MHZ, CDCl$_3$) δ 4.06 (t, J=6.8 Hz, 2H), 3.97 (d, J=5.8 Hz, 2H), 3.66-3.64 (m, 2H), 2.42 (t, J=6.2 Hz, 6H), 2.32 (q, J=7.1 Hz, 4H), 1.88-1.76 (m, 5H), 1.68-1.58 (m, 7H), 1.37-1.20 (m, 44H), 0.88 (t, J=6.8 Hz, 9H).

3. Synthesis of 2-octyldecyl 6-((6-(decyloxy)-6-oxohexyl)(2-hydroxyethyl)amino)hexanoate (YK-003)

The synthetic route is as follows:

Step 2: Synthesis of n-decyl 6-((2-hydroxyethyl)amino)hexanoate (YK-003-PM2)

n-Decyl 6-bromohexanoate (1.12 g, 3.34 mmol) and ethanolamine (8.20 g, 134.25 mmol) were dissolved in ethanol (15 mL), and reacted with stirring at room temperature for 16 hours. The reaction solution was concentrated under reduced pressure in vacuo to remove the solvent, then diluted with ethyl acetate (80 mL), and washed with saturated brine (50 ml×3). The organic phase was concentrated under reduced pressure and purified by silica gel chromatography to give n-decyl 6-((2-hydroxyethyl)amino)hexanoate (0.66 g, 2.09 mmol, 62.6%). $C_{18}H_{37}NO_3$. MS (ES): m/z (M+H$^+$) 316.3.

$^1$H NMR (400 MHZ, CDCl$_3$) δ 4.05 (t, J=6.8 Hz, 2H), 3.93-3.88 (m, 1H), 3.72-3.70 (m, 1H), 3.66-3.56 (m, 1H), 3.55-3.50 (m, 1H), 3.34 (s, 2H), 2.83 (d, J=5.1 Hz, 1H), 2.72-2.68 (m, 1H), 2.31 (t, J=7.4 Hz, 2H), 1.69-1.54 (m, 6H), 1.35-1.21 (m, 16H), 0.88 (t, J=6.9 Hz, 3H).

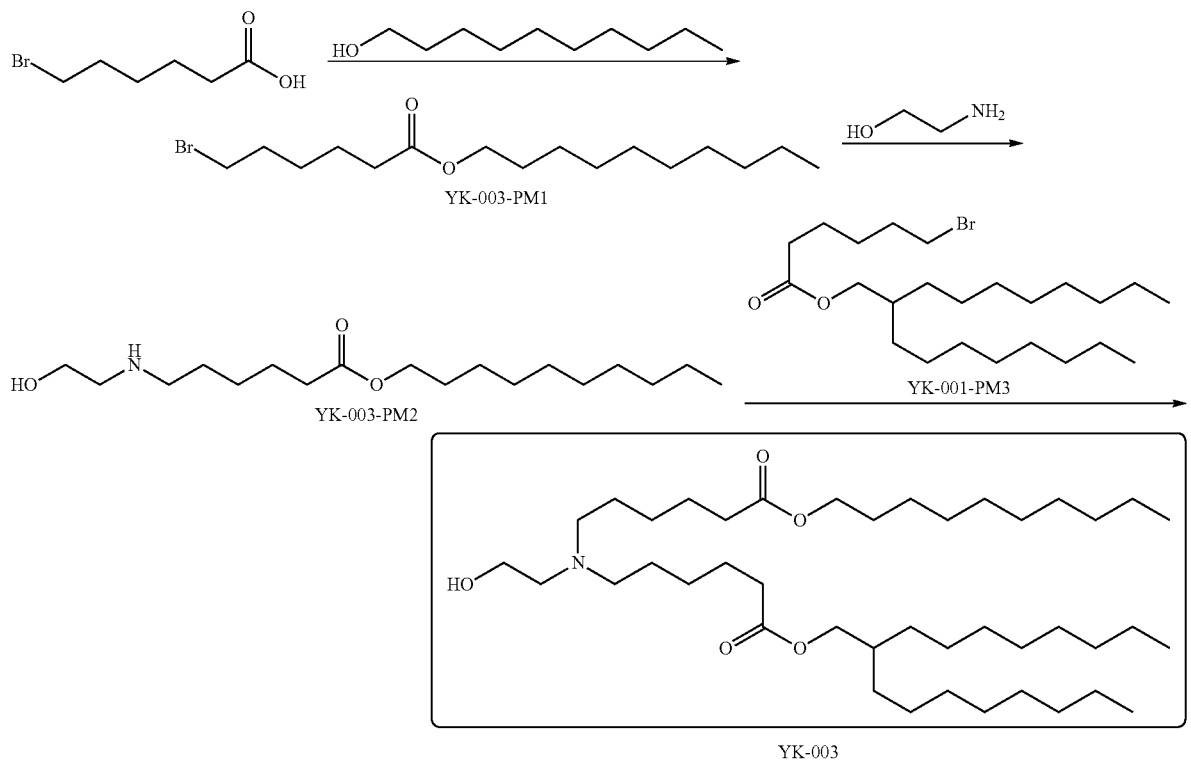

Step 1: Synthesis of n-decyl 6-bromohexanoate (YK-003-PM1)

According to the method for preparing YK-001-PM1, 6-bromohexanoic acid (1.95 g, 10.00 mmol) and n-decanol (1.45 g, 9.16 mmol) were used as raw materials to give n-decyl 6-bromohexanoate (2.41 g, 7.19 mmol, 78.49%).

$^1$H NMR (400 MHZ, CDCl$_3$) δ 4.06 (t, J=6.7 Hz, 2H), 3.41 (t, J=6.8 Hz, 2H), 2.32 (t, J=7.4 Hz, 2H), 1.94-1.81 (m, 2H), 1.73-1.56 (m, 3H), 1.54-1.41 (m, 2H), 1.39-1.19 (m, 15H), 0.88 (t, J=6.9 Hz, 3H).

Step 3 Synthesis of 2-octyldecyl 6-((6-(decyloxy)-6-oxohexyl)(2-hydroxyethyl)amino)hexanoate (YK-003)

According to the method for preparing YK-001, n-decyl 6-((2-hydroxyethyl)amino)hexanoate (157 mg, 0.50 mmol) and 2-octyldecyl 6-bromohexanoate (226 mg, 0.50 mmol) were used as raw materials to give the target compound (140 mg, 0.21 mmol, 42.00%). $C_{42}H_{83}NO_5$, MS (ES): m/z (M+H$^+$) 682.8.

$^1$H NMR (400 MHZ, CDCl$_3$) δ 4.06 (t, J=6.8 Hz, 2H), 3.97 (d, J=5.8 Hz, 2H), 3.72 (q, J=7.0 Hz, 1H), 3.64 (t, J=6.6

Hz, 1H), 2.32 (td, J=7.4, 2.4 Hz, 5H), 1.73-1.54 (m, 14H), 1.41-1.19 (m, 49H), 0.89 (d, J=6.6 Hz, 9H).

4. Synthesis of 2-octyldecyl 4-((4-(decyloxy)-4-oxobutyl)(2-hydroxyethyl)amino)butyrate (YK-004)

The synthetic route is as follows:

$^1$H NMR (400 MHZ, CDCl$_3$) δ 3.76 (t, J=5.2 Hz, 2H), 3.62 (dd, J=8.3, 4.9 Hz, 4H), 3.50 (t, J=7.1 Hz, 2H), 3.45-3.36 (m, 2H), 2.91-2.76 (m, 2H), 2.44 (d, J=8.0 Hz, 2H), 2.08 (dd, J=15.1, 7.5 Hz, 2H), 1.67-1.51 (m, 2H), 1.27 (s, 12H), 0.88 (t, J=6.5 Hz, 3H).

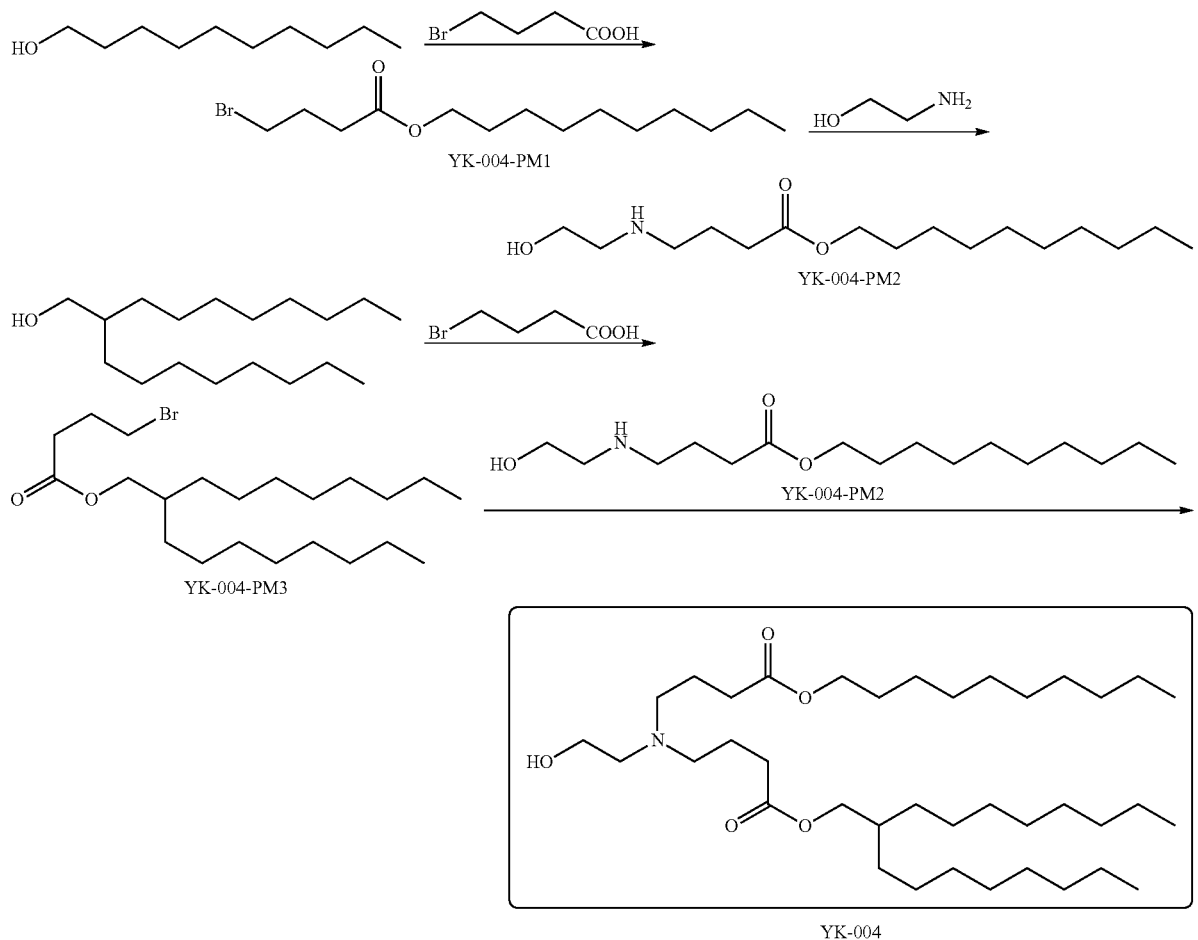

Step 1: Synthesis of n-decyl 4-bromobutyrate (YK-004-PM1)

According to the method for preparing YK-001-PM1, 4-bromobutyric acid (15.00 g, 89.82 mmol) and 1-decanol (12.90 g, 81.50 mmol) were used as raw materials to give n-decyl 4-bromobutyrate (10.52 g, 34.2 mmol, 42.0%).

$^1$H NMR (400 MHZ, CDCl$_3$) δ 4.07 (d, J=6.8 Hz, 2H), 3.47 (t, J=6.5 Hz, 2H), 2.50 (t, J=7.2 Hz, 2H), 2.18 (dd, J=12.5, 5.5 Hz, 2H), 1.62 (t, J=7.2 Hz, 2H), 1.30-1.20 (m, 14H), 0.88 (t, J=6.9 Hz, 3H).

Step 2: Synthesis of n-decyl 4-((2-hydroxyethyl)amino)butyrate (YK-004-PM2)

According to the method of preparing YK-001-PM2, n-decyl 4-bromobutyrate (8.00 g, 26.04 mmol) and ethanolamine (4.78 g, 78.26 mmol) were used as raw materials to give n-decyl 4-((2-hydroxyethyl)amino)butyrate (4.40 g, 15.3 mmol, 58.8%). C$_{16}$H$_{33}$NO$_3$, MS (ES): m/z (M+H$^+$) 288.2.

Step 3: Synthesis of 2-heptylnonyl 4-bromobutyrate (YK-004-PM3)

According to the method for preparing YK-001-PM1, 2-heptylnonanol (390 mg, 1.45 mmol) and 4-bromobutyric acid (265 mg, 1.59 mmol) were used as raw materials to give 2-heptylnonyl 4-bromobutyrate (500 mg, 1.19 mmol, 82.07%).

$^1$H NMR (400 MHZ, CDCl$_3$) δ 3.99 (d, J=5.8 Hz, 2H), 3.47 (t, J=6.5 Hz, 2H), 2.51 (t, J=7.2 Hz, 2H), 2.18 (t, J=6.9 Hz, 2H), 1.29 (d, J=21.2 Hz, 29H), 0.88 (t, J=6.8 Hz, 6H).

Step 4: Synthesis of 2-octyldecyl 4-((4-(decyloxy)-4-oxobutyl)(2-hydroxyethyl)amino)butyrate (YK-004)

According to the method for preparing YK-001, 2-heptylnonyl 4-bromobutyrate (250 mg, 0.60 mmol) and n-decyl 4-((2-hydroxyethyl)amino)butyrate (172 mg, 0.60 mmol)

were used as raw materials to give the target compound (50 mg, 0.081 mmol, 13.3%). $C_{38}H_{75}NO_5$, MS (ES): m/z (M+H$^+$) 626.6.

$^1$H NMR (400 MHZ, CDCl$_3$) δ 4.06 (t, J=6.8 Hz, 2H), 3.97 (d, J=5.9 Hz, 2H), 3.61-3.58 (m, 2H), 2.33 (t, J=6.9 Hz, 4H), 1.81 (s, 3H), 1.65-1.55 (m, 3H), 1.35-1.18 (m, 50H), 0.87 (d, J=7.0 Hz, 9H).

5. Synthesis of 9-heptadecyl 8-((4-(decyloxy)-4-oxobutyl)(2-hydroxyethyl)amino)octanoate (YK-005)

The synthetic route is as follows:

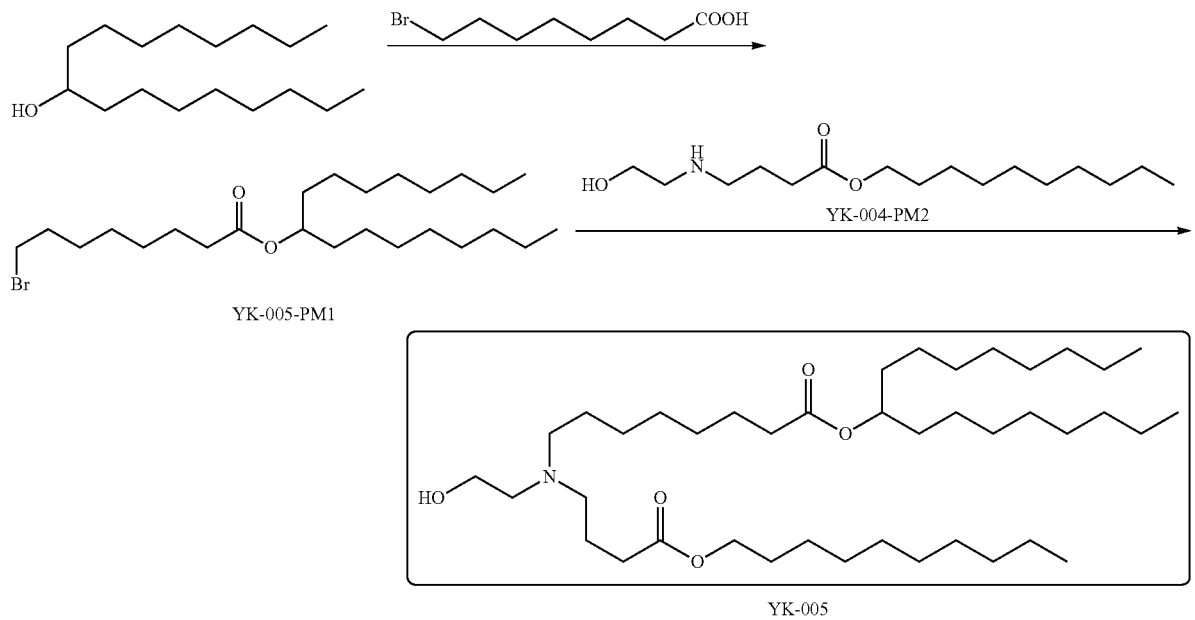

Step 1: Synthesis of 9-heptadecyl 8-bromooctanoate (YK-005-PM1)

According to the method for preparing YK-001-PM1, 8-bromooctanoic acid (2.87 g, 12.86 mmol) and 9-heptadecanol (3.00 g, 11.70 mmol) were used as raw materials to give 9-heptadecyl 8-bromooctanoate (3.15 g, 6.82 mmol, 58.3%).

Step 2: Synthesis of 9-heptadecyl 8-((4-(decyloxy)-4-oxobutyl)(2-hydroxyethyl)amino)octanoate (YK-005)

According to the method for preparing YK-001, n-decyl 4-((2-hydroxyethyl)amino)butyrate (150 mg, 0.52 mmol) and 9-heptadecyl 8-bromooctanoate (285 mg, 0.62 mmol) were used as raw materials to give the target compound (140 mg, 0.21 mmol, 40.4%). $C_{41}H_{81}NO_5$, MS (ES): m/z (M+H$^+$) 668.6.

$^1$H NMR (400 MHZ, CDCl$_3$) δ 4.06 (t, J=6.8 Hz, 2H), 3.63 (t, J=5.0 Hz, 2H), 2.71 (t, J=4.8 Hz, 2H), 2.67-2.54 (m, 4H), 2.35 (t, J=7.1 Hz, 2H), 2.28 (t, J=7.5 Hz, 2H), 1.89-1.80 (m, 2H), 1.61 (dd, J=12.7, 5.9 Hz, 5H), 1.50 (d, J=5.9 Hz, 6H), 1.38-1.18 (m, 45H), 0.90-0.84 (m, 9H).

6. Synthesis of 5-((4-(decyloxy)-4-oxobutyl)(2-hydroxyethyl)amino)pentanoate (YK-006) 2-octyldecyl The synthetic route is as follows:

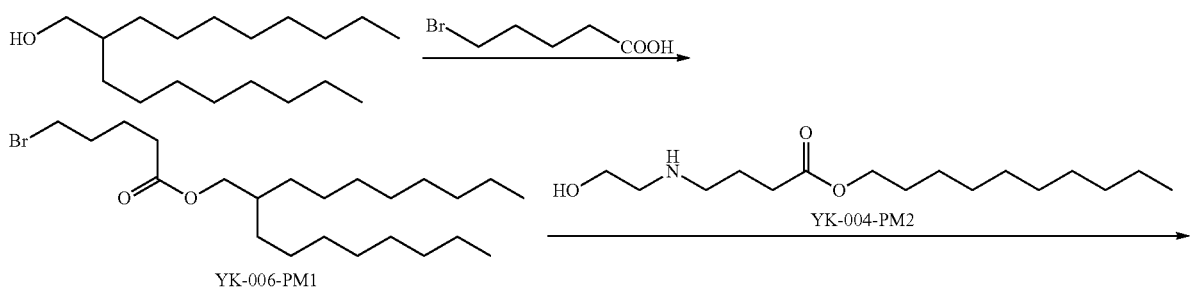

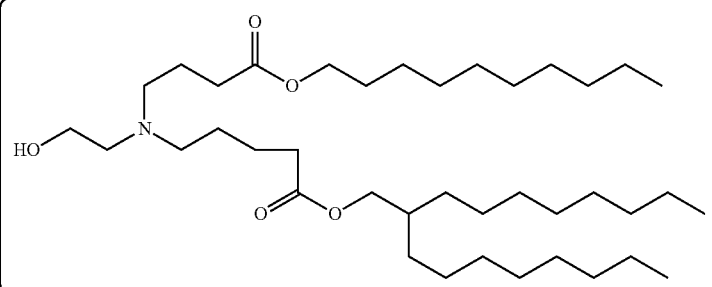

YK-006

Step 1: Synthesis of 2-heptylnonyl 5-bromopentanoate (YK-006-PM1)

According to the method for preparing YK-001-PM1, 2-heptylnonanol (300 mg, 1.11 mmol) and 5-bromopentanoic acid (220 mg, 1.22 mmol) were used as raw materials to give 2-heptylnonyl 5-bromopentanoate (438 mg, 1.01 mmol, 91.0%).

$^1$H NMR (400 MHZ, CDCl$_3$) δ 3.98 (d, J=5.8 Hz, 2H), 3.41 (t, J=6.6 Hz, 2H), 2.35 (t, J=7.2 Hz, 2H), 1.90 (ddd, J=13.6, 7.7, 3.7 Hz, 2H), 1.84-1.72 (m, 2H), 1.29 (d, J=21.6 Hz, 29H), 0.88 (t, J=6.8 Hz, 6H).

Step 2 Synthesis of 2-octyldecyl 5-((4-(decyloxy)-4-oxobutyl)(2-hydroxyethyl)amino)pentanoate (YK-006)

According to the method for preparing YK-001, 2-heptylnonyl 5-bromopentanoate (200 mg, 0.46 mmol) and n-decyl 4-((2-hydroxyethyl)amino)butyrate (133 mg, 0.46 mmol) were used as raw materials to give the target compound (65 mg, 0.10 mmol, 21.7%). C$_{39}$H$_{77}$NO$_5$, MS (ES): m/z (M+H$^+$) 640.6.

$^1$H NMR (400 MHZ, CDCl$_3$) δ 4.06 (t, J=6.8 Hz, 2H), 3.97 (d, J=5.8 Hz, 2H), 3.55-3.50 (m, 2H), 2.65-2.45 (m, 3H) 2.33 (t, J=6.7 Hz, 4H), 2.01 (s, 1H), 1.61 (d, J=6.8 Hz, 10H), 1.39-1.10 (m, 44H), 0.88 (t, J=6.8 Hz, 9H).

7. Synthesis of 6-((2-hydroxyethyl)(6-oxo-6-(undecyloxy)hexyl)amino)hexanoate (YK-007) 2-octyldecyl The synthetic route is as follows:

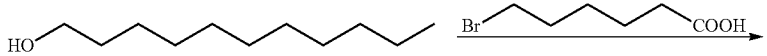

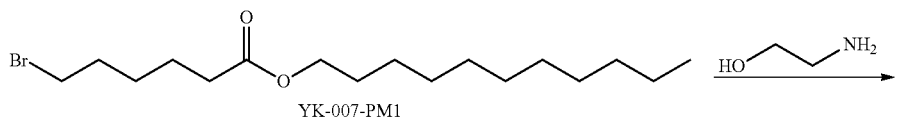

YK-007-PM1

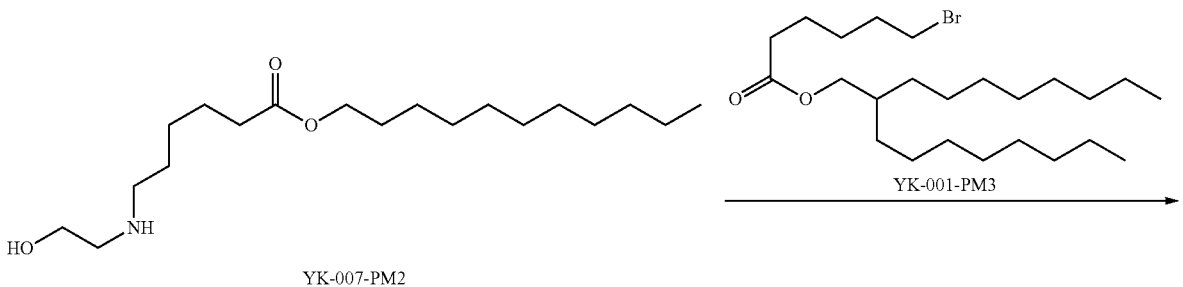

YK-007-PM2

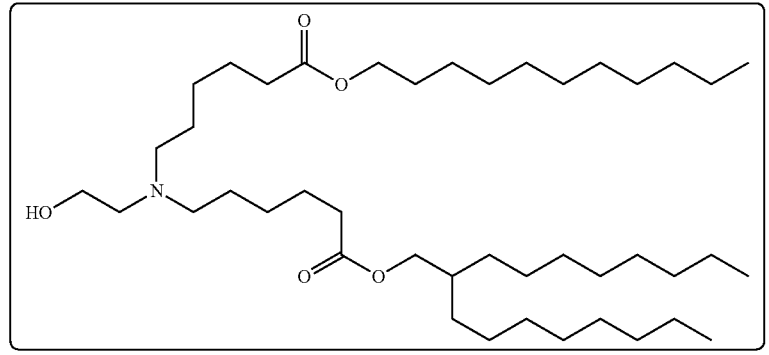
YK-007

Step 1: Synthesis of 1-undecyl 6-bromohexanoate (YK-007-PM1)

According to the method for preparing YK-001-PM1, 6-bromohexanoic acid (2.50 g, 12.82 mmol) and 1-undecyl alcohol (2.00 g, 11.61 mmol) were used as raw materials to give 1-undecyl 6-bromohexanoate (2.40 g, 6.87 mmol, 59.2%).

Step 2: Synthesis of undecyl 6-((2-hydroxyethyl)amino)hexanoate (YK-007-PM2)

According to the method for preparing YK-001-PM2, 1-undecyl 6-bromohexanoate (2.25 g, 6.44 mmol) and ethanolamine (1.18 g, 19.29 mmol) were used as raw materials to give undecyl 6-((2-hydroxyethyl)amino)hexanoate (855 mg, 2.59 mmol, 40.2%). $C_{19}H_{39}NO_3$, MS (ES): m/z (M+H$^+$) 330.3.

Step 3 Synthesis of 2-octyldecyl 6-((2-hydroxyethyl)(6-oxo-6-(undecyloxy)hexyl)amino)hexanoate (YK-007)

According to the method for preparing YK-001, undecyl 6-((2-hydroxyethyl)amino)hexanoate (300 mg, 0.91 mmol) and 2-octyldecyl 6-bromohexanoate (488 mg, 1.09 mmol) were used as raw materials to give the target compound (260 mg, 0.37 mmol, 41.1%). $C_{43}H_{85}NO_5$, MS (ES): m/z (M+H$^+$) 696.6.

$^1$H NMR (400 MHZ, CDCl$_3$) δ 4.09-4.02 (m, 2H), 3.97 (d, J=5.8 Hz, 2H), 3.53-3.48 (m, 2H), 2.35-2.29 (m, 4H), 2.01 (dd, J=12.6, 6.9 Hz, 2H), 1.74-1.55 (m, 6H), 1.28 (d, J=14.7 Hz, 58H), 0.89 (d, J=6.5 Hz, 9H).

8. Synthesis of 6-((4-(nonyloxy)-4-oxobutyl)(2-hydroxyethyl)amino)hexanoate (YK-008) 2-octyldecyl The synthetic route is as follows:

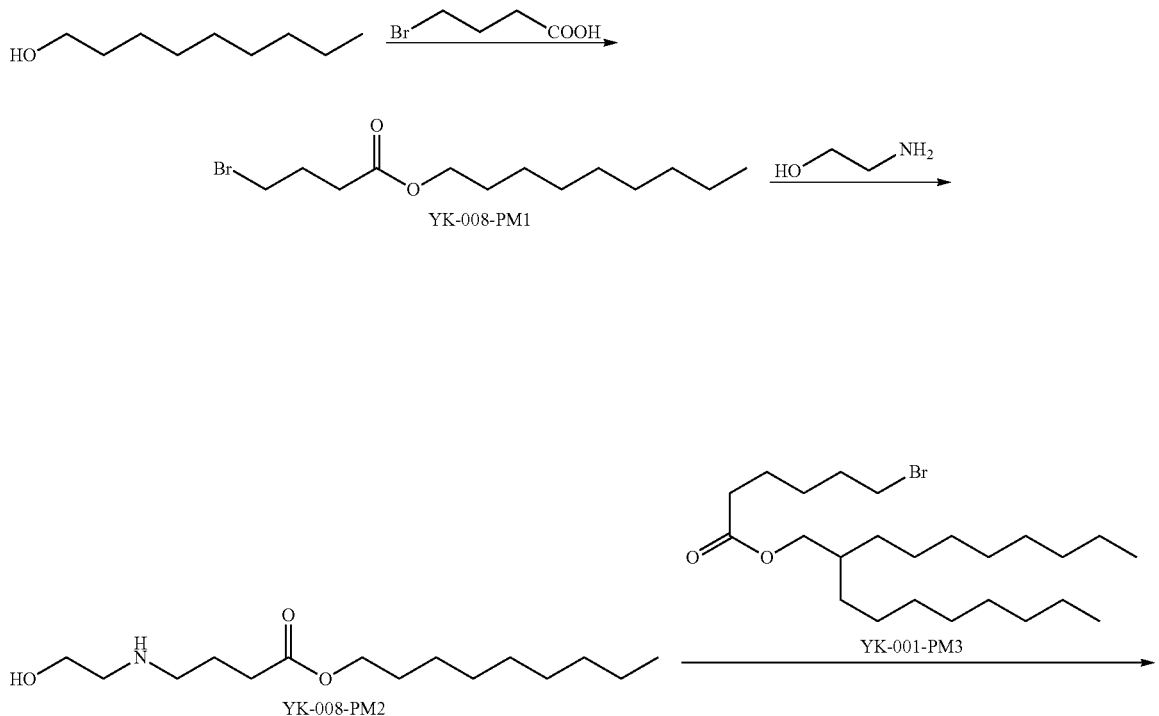

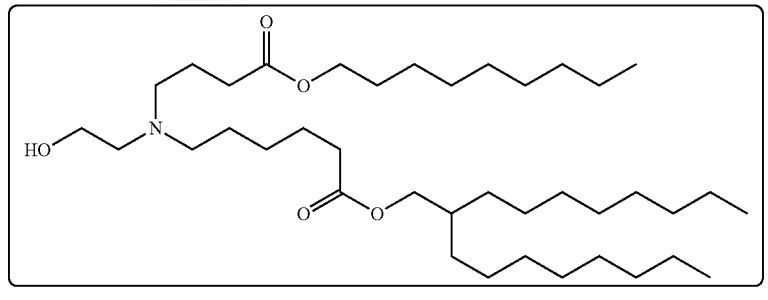

YK-008

Step 1: Synthesis of n-nonyl 4-bromobutyrate (YK-008-PM1)

According to the method for preparing YK-001-PM1, n-nonanol (5.00 g, 34.66 mmol) and 4-bromobutyric acid (6.11 g, 36.59 mmol) were used as raw materials to give n-nonyl 4-bromobutyrate (3.66 g, 12.5 mmol, 36.0%).

$^1$H NMR (400 MHZ, CDCl$_3$) δ 4.08 (t, J=6.8 Hz, 2H), 3.47 (t, J=6.5 Hz, 2H), 2.50 (t, J=7.2 Hz, 2H), 2.18 (p, J=6.7 Hz, 2H), 1.61 (dd, J=14.1, 7.0 Hz, 2H), 1.40-1.19 (m, 12H), 0.88 (t, J=6.9 Hz, 3H).

Step 2: Synthesis of n-nonyl 4-((2-hydroxyethyl)amino)butyrate (YK-008-PM2)

According to the method for preparing YK-001-PM2, n-nonyl 4-bromobutyrate (2.46 g, 8.39 mmol) and ethanolamine (1.28 g, 20.96 mmol) were used as raw materials to give n-nonyl 4-((2-hydroxyethyl)amino)butyrate (1.22 g, 4.46 mmol, 53.2%), C$_{15}$H$_{31}$NO$_3$, MS (ES): m/z (M+H$^+$) 274.2.

$^1$H NMR (400 MHZ, CDCl$_3$) δ 4.06 (t, J=6.8 Hz, 2H), 3.53-3.47 (m, 3H), 2.68 (t, J=7.0 Hz, 2H), 2.43 (t, J=8.1 Hz, 2H), 2.37 (s, 1H), 2.12-2.01 (m, 2H), 1.83 (m, 2H), 1.67-1.51 (m, 2H), 1.40-1.21 (m, 10H), 0.88 (t, J=6.9 Hz, 3H).

Step 3 Synthesis of 2-octyldecyl 6-((4-(nonyloxy)-4-oxobutyl)(2-hydroxyethyl)amino)hexanoate (YK-008)

According to the method for preparing YK-001, 2-octyldecyl 6-bromohexanoate (200 mg, 0.45 mmol) and n-nonyl 4-((2-hydroxyethyl)amino)butyrate (102 mg, 0.37 mmol) were used as raw materials to give the target compound (30 mg, 0.047 mmol, 13.5%). C$_{39}$H$_{77}$NO$_5$, MS (ES): m/z (M+H$^+$) 640.6.

$^1$H NMR (400 MHZ, CDCl$_3$) δ 4.06 (t, J=6.8 Hz, 2H), 3.97 (d, J=5.8 Hz, 2H), 3.68-3.62 (m, 2H), 2.32 (dd, J=15.2, 7.6 Hz, 4H), 1.63 (dd, J=15.1, 7.6 Hz, 6H), 1.39-1.17 (m, 52H), 0.87 (d, J=7.0 Hz, 9H).

9. Synthesis of 2-octyldecyl 6-((4-(decyloxy)-4-oxobutyl)(2-hydroxyethyl)amino)hexanoate (YK-009)

The synthetic route is as follows:

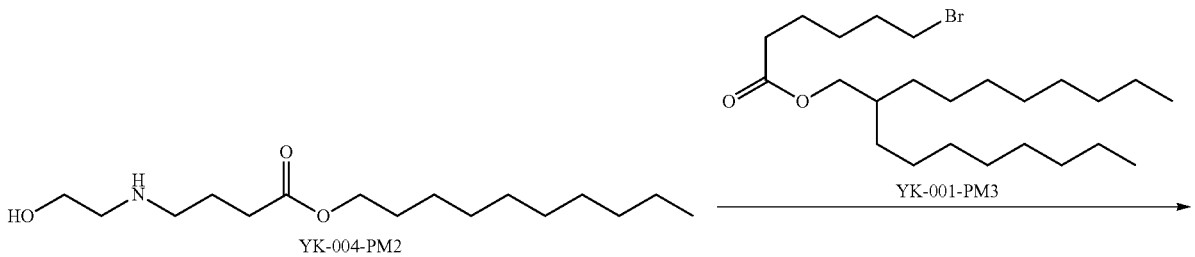

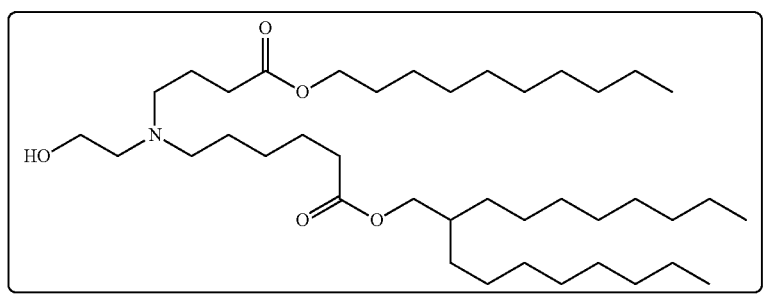

YK-009

Step 1: Synthesis of 2-octyldecyl 6-((4-(decyloxy)-4-oxobutyl)(2-hydroxyethyl)amino)hexanoate (YK-009)

According to the method for preparing YK-001, n-decyl 4-((2-hydroxyethyl)amino)butyrate (1.00 g, 3.48 mmol) and 2-octyldecyl 6-bromohexanoate (1.87 g, 4.18 mmol) were used as raw materials to give the target compound (0.92 g, 1.41 mmol, 40.5%). $C_{40}H_{79}NO_5$, MS (ES): m/z (M+H$^+$) 654.6.

$^1$H NMR (400 MHZ, CDCl$_3$) δ 4.07 (t, J=6.8 Hz, 4H), 3.96 (d, J=5.8 Hz, 2H), 2.49 (t, J=5.7 Hz, 2H), 2.34 (t, J=7.3 Hz, 2H), 2.27-2.17 (m, 2H), 2.01 (d, J=5.7 Hz, 2H), 1.68-1.62 (m, 9H), 1.46-1.43 (m, 3H), 1.36-1.15 (m, 44H), 0.87 (d, J=7.0 Hz, 9H).

10. Synthesis of 2-heptylnonyl 6-((4-(decyloxy)-4-oxobutyl)(2-hydroxyethyl)amino)hexanoate (YK-010)

The synthetic route is as follows:

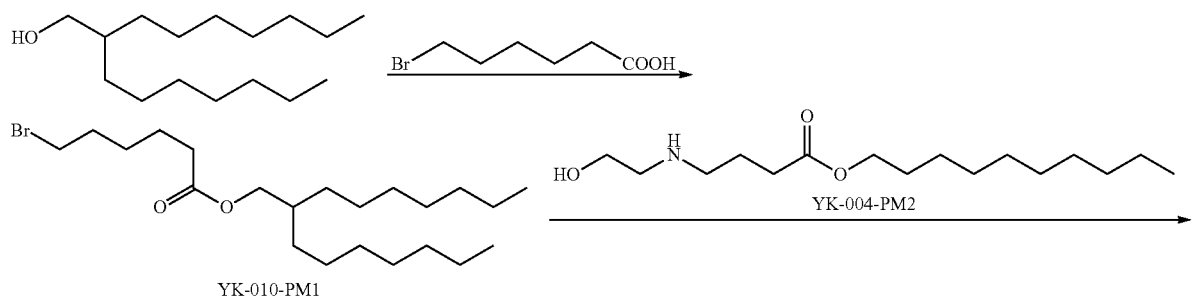

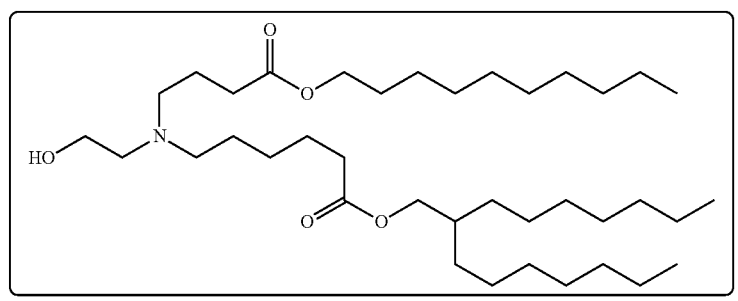

Step 1: Synthesis of 2-heptylnonyl 6-bromohexanoate (YK-010-PM1)

According to the method for preparing YK-001-PM1, 6-bromohexanoic acid (290 mg, 1.49 mmol) and 2-heptylnonanol (300 mg, 1.24 mmol) were used as raw materials to give 2-heptylnonyl 6-bromohexanoate (280 mg, 0.67 mmol, 54.0%).

$^1$H NMR (400 MHZ, CDCl$_3$) δ 3.97 (d, J=5.8 Hz, 2H), 3.41 (t, J=6.8 Hz, 2H), 2.33 (t, J=7.4 Hz, 2H), 1.93-1.84 (m, 2H), 1.66 (dt, J=20.5, 7.4 Hz, 3H), 1.52-1.43 (m, 2H), 1.36-1.20 (m, 24H), 0.88 (t, J=6.9 Hz, 6H).

Step 2: Synthesis of 2-heptylnonyl 6-((4-(decyloxy)-4-oxobutyl)(2-hydroxyethyl)amino)hexanoate (YK-010)

According to the method for preparing YK-001, n-decyl 4-((2-hydroxyethyl)amino)butyrate (150 mg, 0.52 mmol) and 2-heptylnonyl 6-bromohexanoate (260 mg, 0.62 mmol) were used as raw materials to give the target compound (150 mg, 0.24 mmol, 46.2%). $C_{38}H_{75}NO_5$, MS (ES): m/z (M+H$^+$) 626.7.

$^1$H NMR (400 MHZ, CDCl$_3$) δ 4.27 (qd, J=11.0, 5.8 Hz, 2H), 4.13-4.01 (m, 2H), 3.97 (d, J=5.8 Hz, 2H), 2.33 (dt, J=12.5, 7.3 Hz, 4H), 1.86-1.81 (m, 1H), 1.78-1.68 (m, 2H), 1.67-1.59 (m, 4H), 1.33-1.17 (m, 49H), 0.88 (t, J=4.6 Hz, 9H).

11. Synthesis of 2-hexyloctyl 6-((4-(decyloxy)-4-oxobutyl)(2-hydroxyethyl)amino)hexanoate (YK-011)

The synthetic route is as follows:

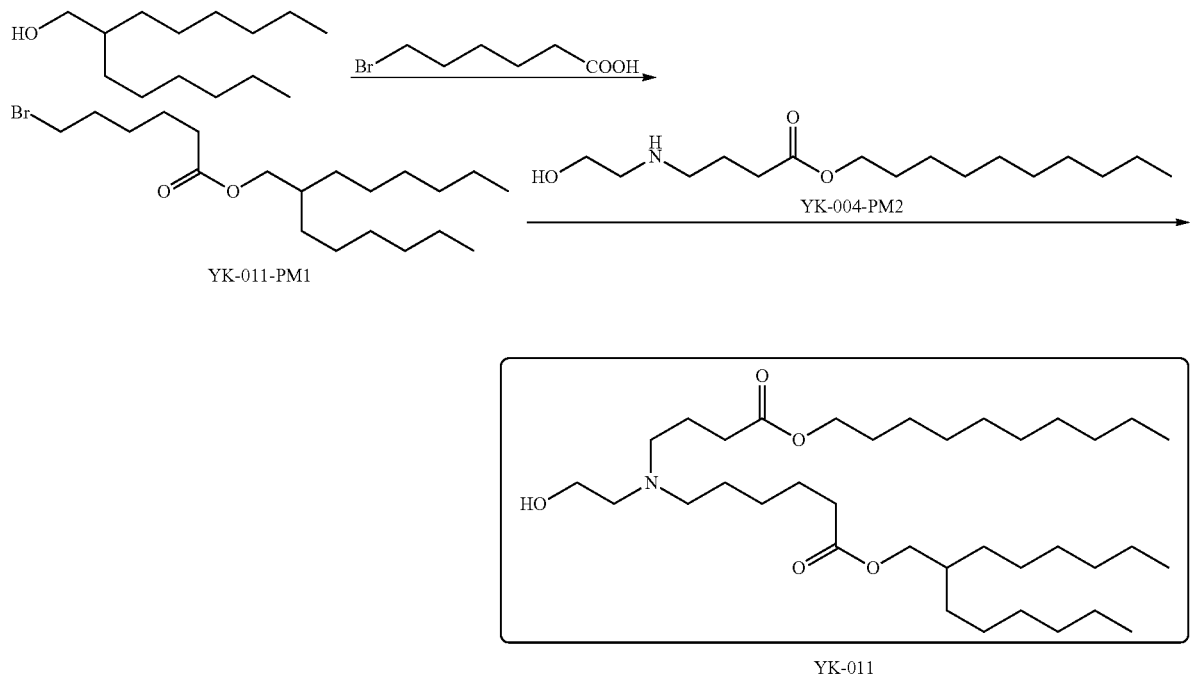

Step 1: Synthesis of 2-hexyloctyl 6-bromohexanoate (YK-011-PM1)

According to the method for preparing YK-001-PM1, 6-bromohexanoic acid (290 mg, 1.49 mmol) and 2-hexyloctanol (300 mg, 1.40 mmol) were used as raw materials to give 2-hexyloctyl 6-bromohexanoate (240 mg, 0.61 mmol, 41.6%).

$^1$H NMR (400 MHZ, CDCl$_3$) δ 3.97 (d, J=5.8 Hz, 2H), 3.41 (t, J=6.8 Hz, 2H), 2.33 (t, J=7.4 Hz, 2H), 1.92-1.83 (m, 2H), 1.66 (dt, J=20.5, 7.4 Hz, 3H), 1.48 (ddd, J=8.6, 6.8, 4.2 Hz, 2H), 1.37-1.20 (m, 20H), 0.88 (t, J=6.8 Hz, 6H).

Step 2: Synthesis of 2-hexyloctyl 6-((4-(decyloxy)-4-oxobutyl)(2-hydroxyethyl)amino)hexanoate (YK-011)

According to the method for preparing YK-001, n-decyl 4-((2-hydroxyethyl)amino)butyrate (150 mg, 0.52 mmol) and 2-hexyloctyl 6-bromohexanoate (240 mg, 0.61 mmol) were used as raw materials to give the target compound (120 mg, 0.20 mmol, 38.5%). C$_{36}$H$_{71}$NO$_5$, MS (ES): m/z (M+H$^+$) 598.5.

$^1$H NMR (400 MHz, CDCl$_3$) δ 4.09-4.03 (m, 4H), 3.56-3.53 (m, 2H), 2.41 (t, J=6.8 Hz, 2H), 2.22 (t, J=7.1 Hz, 2H), 1.71-1.63 (m, 3H), 1.58-1.54 (m, 2H), 1.42-1.19 (m, 47H), 0.88 (t, J=6.8 Hz, 9H).

12. Synthesis of nonyl 8-((2-hydroxyethyl)(10-((9-heptadecyl)oxy)-10-oxodecyl)amino)octanoate (compound 23)

The synthetic route is as follows:

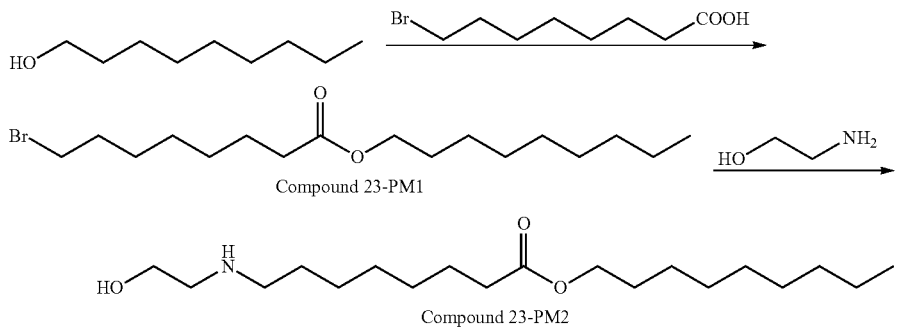

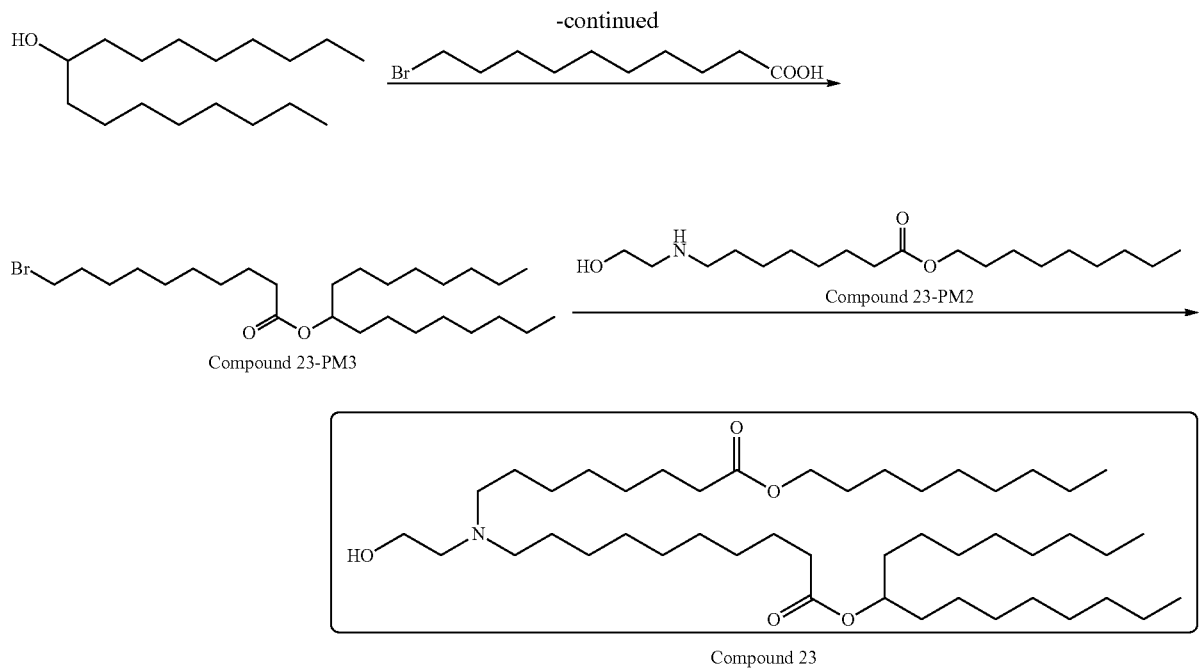

Compound 23

Step 1: Synthesis of n-nonyl 8-bromooctanoate (Compound 23-PM1)

According to the method for preparing YK-001-PM1, 8-bromooctanoic acid (2.50 g, 11.21 mmol) and n-nonanol (1.47 g, 10.19 mmol) were used as raw materials to give n-nonyl 8-bromooctanoate (1.85 g, 5.30 mmol, 52.0%).

Step 2: Synthesis of nonyl 8-((2-hydroxyethyl)amino)octanoate (Compound 23-PM2)

According to the method for preparing YK-001-PM2, n-nonyl 8-bromooctanoate (1.50 g, 4.29 mmol) prepared above and ethanolamine (7.96 g, 130.32 mmol) were used as raw materials to give nonyl 8-((2-hydroxyethyl)amino)octanoate (610 mg, 1.85 mmol, 43.1%). $C_{19}H_{39}NO_3$, MS (ES): m/z (M+H$^+$) 330.3.

Step 3: Synthesis of 9-heptadecyl 10-bromodecanoate (Compound 23-PM3)

According to the method for preparing YK-001-PM1, 10-bromodecanoic acid (3.23 g, 12.86 mmol) and 9-heptadecanol (3.00 g, 11.70 mmol) were used as raw materials to give 9-heptadecyl 10-bromodecanoate (3.10 g, 6.72 mmol, 57.4%).

Step 4: Synthesis of nonyl 8-(10-((9-heptadecyl)oxy)-10-oxodecyl)amino)octanoate (Compound 23)

According to the method for preparing YK-001, nonyl 8-((2-hydroxyethyl)amino)octanoate (500 mg, 1.52 mmol) and 9-heptadecyl 10-bromodecanoate (840 mg, 1.72 mmol) were used as raw materials to give the target compound (520 mg, 0.70 mmol, 46.1%). $C_{46}H_{91}NO_5$, MS (ES): m/z (M+H$^+$) 738.8.

$^1$H NMR (400 MHZ, CDCl$_3$) δ 4.88-4.86 (m, 1H), 4.05 (t, J=6.8 Hz, 2H), 3.97 (d, J=5.8 Hz, 2H), 2.77-2.69 (m, 5H), 2.25 (m, 4H), 1.61 (dd, J=13.5, 6.6 Hz, 13H), 1.38-1.18 (m, 55H), 0.88 (t, J=6.8 Hz, 9H).

13. Synthesis of nonyl 8-((2-hydroxyethyl)(6-((9-heptadecyl)oxy)-6-oxohexyl)amino)octanoate (Compound 27)

The synthetic route is as follows:

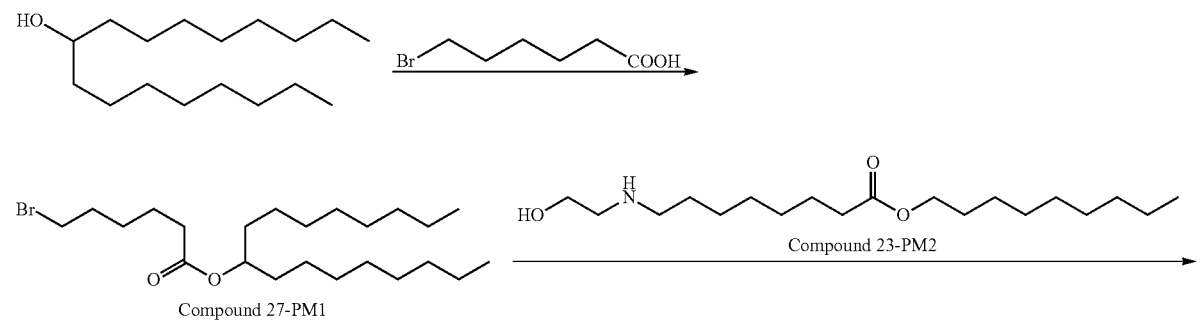

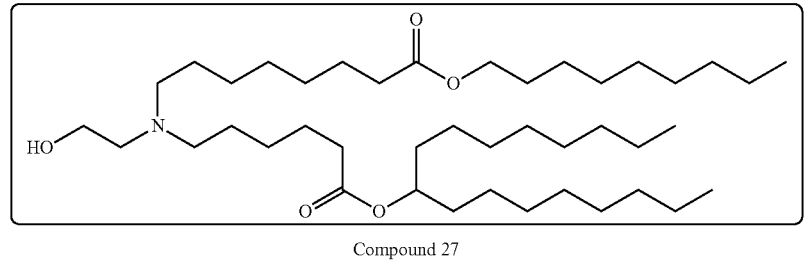

Compound 27

Step 1: Synthesis of 9-heptadecyl 6-bromohexanoate (Compound 27-PM1)

According to the method for preparing YK-001-PM1, 6-bromohexanoic acid (2.51 g, 12.87 mmol) and 9-heptadecanol (3.00 g, 11.70 mmol) were used as raw materials to give 9-heptadecyl 6-bromohexanoate (2.77 g, 6.39 mmol, 54.6%).

Step 2: Synthesis of nonyl 8-(6-((9-heptadecyl)oxy)-6-oxohexyl)amino)octanoate (Compound 27)

According to the method for preparing YK-001, nonyl 8-((2-hydroxyethyl)amino)octanoate (500 mg, 1.52 mmol) and 9-heptadecyl 6-bromohexanoate (760 mg, 1.75 mmol) were used as raw materials to give the target compound (471 mg, 0.69 mmol, 45.4%). $C_{42}H_{83}NO_5$, MS (ES): m/z (M+H$^+$) 682.6.

$^1$H NMR (400 MHZ, CDCl$_3$) δ 4.83-4.81 (m, 1H), 4.05-4.00 (m, 2H), 3.77-3.69 (m, 2H), 2.75-2.59 (m, 5H), 2.25-2.19 (m, 4H), 1.59 (dd, J=13.3, 6.3 Hz, 13H), 1.34-1.03 (m, 47H), 0.87 (t, J=6.7 Hz, 9H).

Example 2: Optimization of Preparation Conditions for Lipid Nanoparticles (LNP Formulations)

1. Optimization of the Ratio of Carrier (Liposome) to mRNA

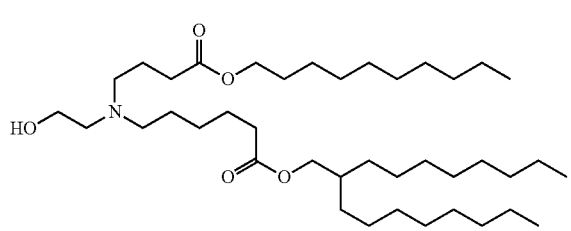

YK-009

The cationic lipid compound YK-009 synthesized in Example 1 was dissolved in ethanol with DSPC (AVT (Shanghai) Pharmaceutical Technology Co., Ltd.), cholesterol (AVT (Shanghai) Pharmaceutical Technology Co., Ltd.) and DMG-PEG2000 according to a molar ratio of 50:10:38.5:1.5, respectively, to prepare an ethanol lipid solution. The ethanol lipid solution was quickly added to citrate buffer (pH=4~5) by ethanol injection method, and vortexed for 30 s for later use. eGFP-mRNA (purchased from Shanghai Biohub International Trade Co., Ltd) was diluted in citrate buffer (pH=4~5) to give an aqueous mRNA solution. A certain volume of liposome solution and mRNA aqueous solution were used to prepare liposomes at a weight ratio of total lipids to mRNA of 4:1, 10:1, 16:1, 24:1, and 30:1, respectively. The mixtures were sonicated at 25° C. for 15 min (with an ultrasonic frequency of 40 kHz and an ultrasonic power of 800 W). The resulting liposomes were diluted to 10 times volume with PBS, and then ultrafiltered with a 300 KDa ultrafiltration tube to remove ethanol. Then the volume was fixed to a certain volume with PBS to give an LNP formulation encapsulating eGFP-mRNA using cationic lipid YK-009/DSPC/cholesterol/DMG-PEG2000 (50:10:38.5:1.5 in molar percentage).

The results of the cell transfection test show that when the weight ratio of carrier to mRNA was in the range of 10:1~30:1, all the transfection effects were good, wherein the ratio of 16:1 had the best transfection effect, and when the weight ratio of carrier to mRNA was 4:1, the transfection effect was poor, and this ratio could not be used to carry mRNA. (FIG. 1)

2. Optimization of the Ratio of Cationic Lipid to Neutral Lipid

The LNP formulation encapsulating eGFP-mRNA was prepared according to the method in 1, wherein the molar ratios of cationic lipid YK-009 and neutral lipid DSPC were 1:1, 5:1 and 10:1, respectively.

Figure 2:
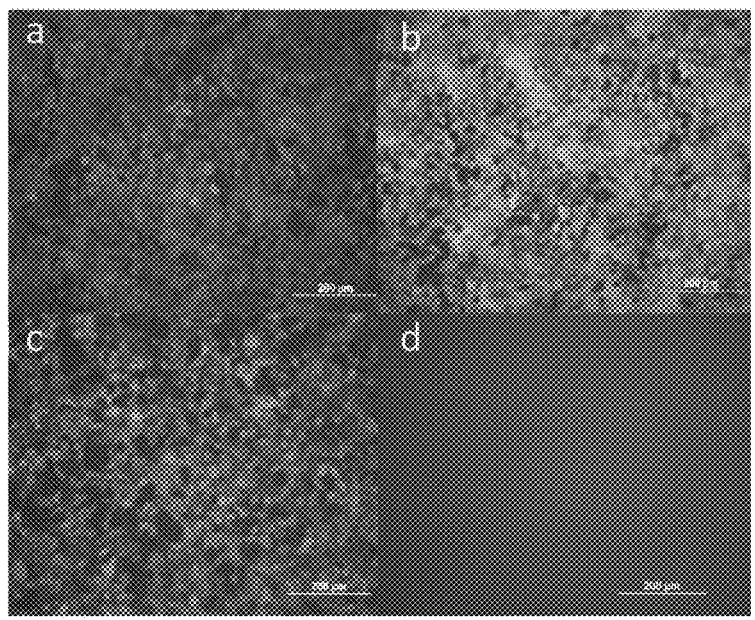
FIG. 2 shows the results of cell transfection tests with different molar ratios of cationic lipid YK-009 to neutral lipid DSPC used in the preparation of LNP formulations, wherein a is 1:1, b is 5:1, c is 10:1, and d is a blank control.

It can be seen from the cell transfection test that when the molar ratio of cationic lipid to neutral lipid was 1:1~10:1, the transfection effect could be achieved, wherein the transfection efficiency was the highest at the molar ratio of cationic lipid to neutral lipid of 5:1. (FIG. 2)

3. Optimization of the Ratio of Polymer-Conjugated Lipid to Carrier (Liposome)

The LNP formulation encapsulating eGFP-mRNA was prepared according to the method in 1, wherein the cationic lipid in the carrier was YK-009, and the molar ratios of the polymer-conjugated lipid DMG-PEG2000 to the carrier were 0.5%, 1.5%, 2.5%, 3.5%, and 5%, respectively.

Figure 3:
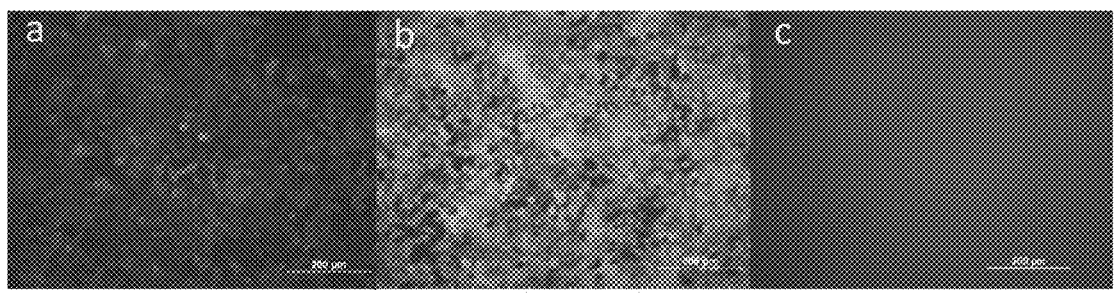
FIG. 3 shows the results of cell transfection tests with different molar ratios of polymer-conjugated lipids to the carrier (including YK-009) in the preparation of LNP formulations, wherein a is 5%, b is 1.5%, and c is a blank control.

The results of the cell transfection test show that when the molar ratio of the polymer-conjugated lipid to the carrier was in the range of 0.5% to 5%, the transfection effect could be achieved, wherein the transfection efficiency was the highest when the molar ratio was 1.5%, and the lowest when the molar ratio was 5%. (FIG. 3)

4. Optimization of the Proportion of Components in the Carrier (Liposome)

The LNP formulation encapsulating eGFP-mRNA was prepared according to the method in 1, wherein the molar ratios of cationic lipid YK-009, neutral lipid DSPC, structured lipid cholesterol and polymer-conjugated lipid DMG-PEG2000 were 65:8:25:2, 50:10:38.5:1.5, 40:17.5:40:2.5 and 25:35:35:5, respectively.

Figure 4:
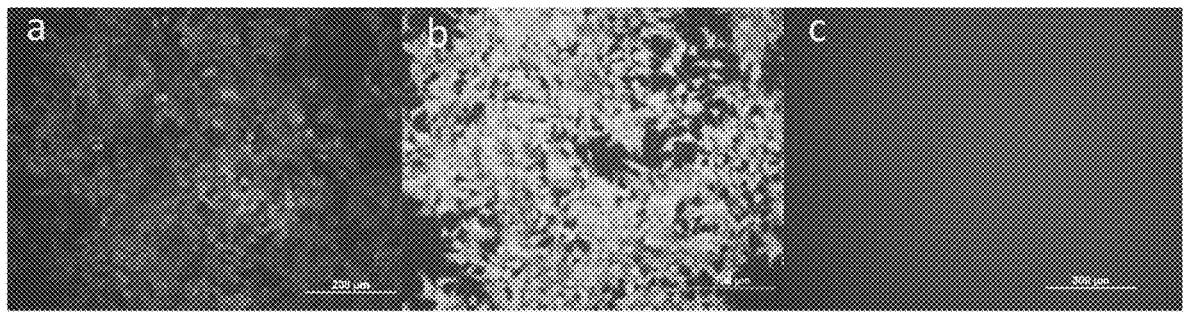
FIG. 4 shows the results of cell transfection tests with different ratios of cationic lipid YK-009, neutral lipid DSPC, structured lipid cholesterol and polymer-conjugated lipid DMG-PEG2000 in the carrier in the preparation of LNP formulations, wherein a is 65:8:25:2, bis 50:10:38.5:1.5, and c is a blank control.

It can be seen from the cell transfection test when the molar ratio of cationic lipid, neutral lipid, structured lipid and polymer-conjugated lipid was 50:10:38.5:1.5, the transfection effect was the best, and when the molar ratio was 65:8:25:2, the transfection effect was worse, but still able to be achieved. (FIG. 4)

Examples 3: Cell Transfection Test of LNP Formulation of eGFP-mRNA

Cell recovery and passage: 293T cells were recovered, cultured in a culture dish, and passaged to the required number of cells.

Seeding plate: The cells in the culture dish were digested and counted. Cells were spread in a 96-well plate at 10,000 cells per well and in a 12-well plate at 150,000 cells per well. Cells were cultured overnight until the cells adhered to the wall.

Cell transfection test: The LNP formulation containing 1.5 μg of eGFP-mRNA prepared in Example 2 (the cationic lipid in the carrier was YK-009) and the Lipofectamin2000 formulation of eGFP-mRNA were added respectively to the cell culture medium of the 12-well plate, and further incubated for 24 hours. The transfection efficiency of different samples was then investigated according to the fluorescence intensity by observing with a fluorescence microscope.

According to the results of the test, the preparation conditions of lipid nanoparticles (LNP formulation) were finally determined: the ratio of carrier to mRNA was 16:1; the molar ratio of cationic lipid to neutral lipid was 5:1; the polymer-conjugated lipid accounted for 1.5% of liposome; the molar ratio of cationic lipid, neutral lipid, structured lipid and polymer-conjugated lipid was 50:10:38.5:1.5, and this condition was used to prepare lipid nanoparticles (LNP formulation) in subsequent tests.

Example 4: Preparation of Lipid Nanoparticles (LNP Formulation) (Optimal Proportion)

TABLE 1

Structure of cationic lipids

| Name | Structure | Remark |
|---|---|---|
| YK-001 | 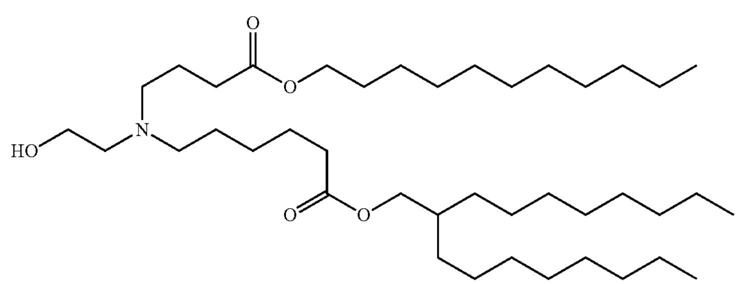 [SMILES: CCCCCCCCCCCOC(=O)CCCN(CCO)CCCCCC(=O)OCC(CCCCCCCC)CCCCCCCC] | Synthesized in Example 1 |
| YK-002 | 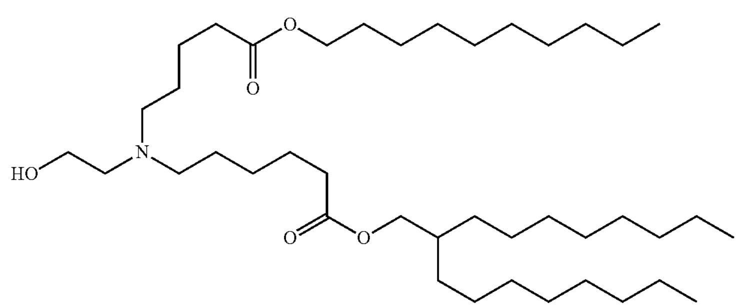 [SMILES: CCCCCCCCCCOC(=O)CCCCN(CCO)CCCCCC(=O)OCC(CCCCCCCC)CCCCCCCC] | Synthesized in Example 1 |
| YK-003 | 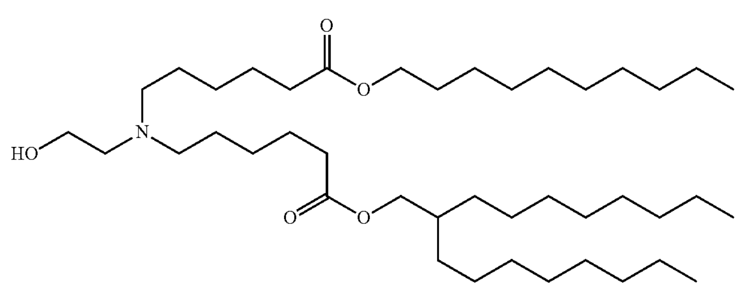 [SMILES: CCCCCCCCCCOC(=O)CCCCCN(CCO)CCCCCC(=O)OCC(CCCCCCCC)CCCCCCCC] | Synthesized in Example 1 |

TABLE 1-continued

Structure of cationic lipids

| Name | Structure | Remark |
|---|---|---|
| YK-004 | 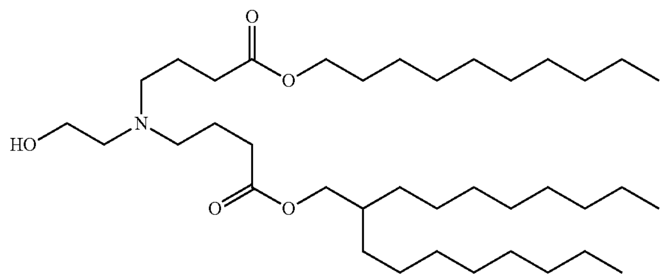 [SMILES: CCCCCCCCCCOC(=O)CCCN(CCO)CCCC(=O)OCC(CCCCCCCC)CCCCCCCC] | Synthesized in Example 1 |
| YK-005 | 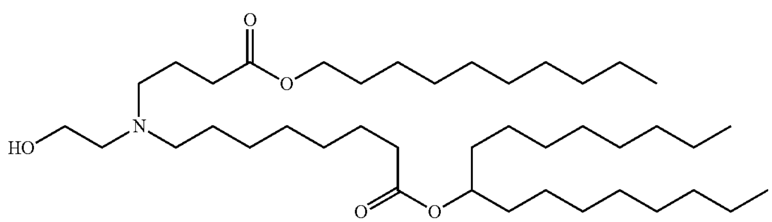 [SMILES: CCCCCCCCCCOC(=O)CCCN(CCO)CCCCCCCC(=O)OC(CCCCCCCC)CCCCCCCC] | Synthesized in Example 1 |
| YK-006 | 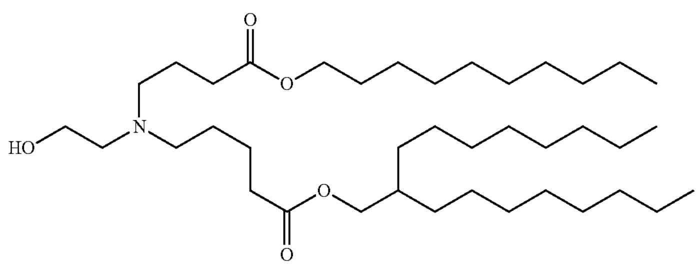 [SMILES: CCCCCCCCCCOC(=O)CCCN(CCO)CCCCC(=O)OCC(CCCCCCCC)CCCCCCCC] | Synthesized in Example 1 |
| YK-007 | 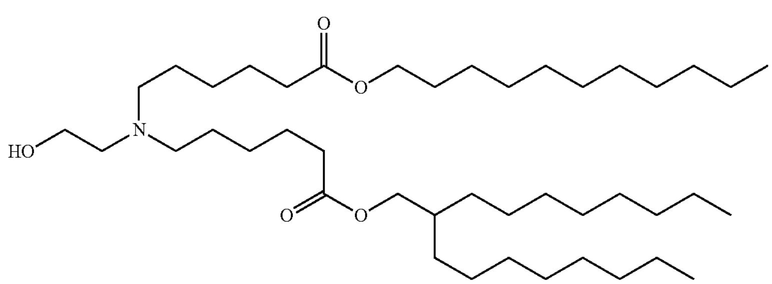 [SMILES: CCCCCCCCCCCOC(=O)CCCCCN(CCO)CCCCCC(=O)OCC(CCCCCCCC)CCCCCCCC] | Synthesized in Example 1 |
| YK-008 | 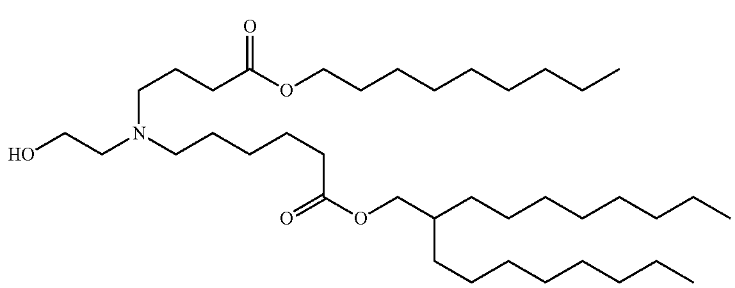 [SMILES: CCCCCCCCCOC(=O)CCCN(CCO)CCCCCC(=O)OCC(CCCCCCCC)CCCCCCCC] | Synthesized in Example 1 |

TABLE 1-continued

Structure of cationic lipids

| Name | Structure | Remark |
|---|---|---|
| YK-009 | 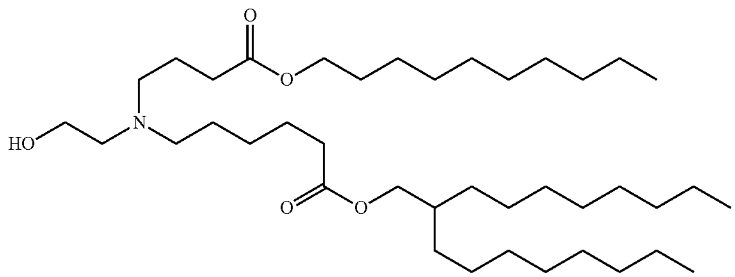 [SMILES: CCCCCCCCCCOC(=O)CCCN(CCO)CCCCCC(=O)OCC(CCCCCCCC)CCCCCCCC] | Synthesized in Example 1 |
| YK-010 | 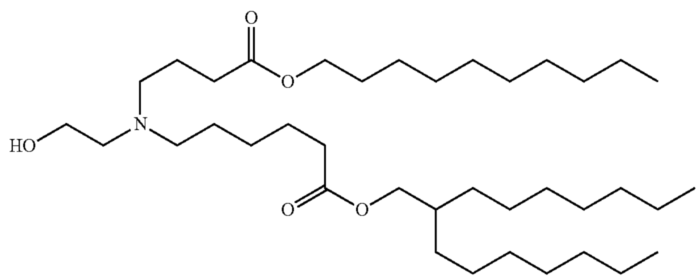 [SMILES: CCCCCCCCCCOC(=O)CCCN(CCO)CCCCCC(=O)OCC(CCCCCCC)CCCCCCC] | Synthesized in Example 1 |
| YK-011 | 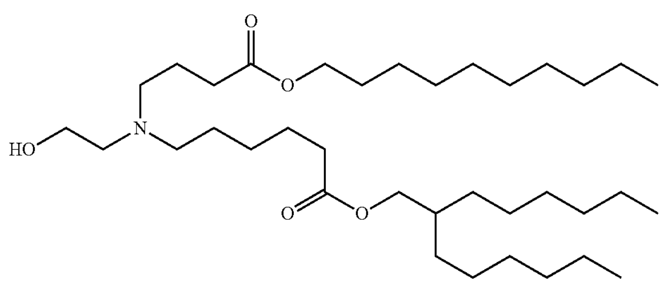 [SMILES: CCCCCCCCCCOC(=O)CCCN(CCO)CCCCCC(=O)OCC(CCCCCC)CCCCCC] | Synthesized in Example 1 |
| Compound 23 | 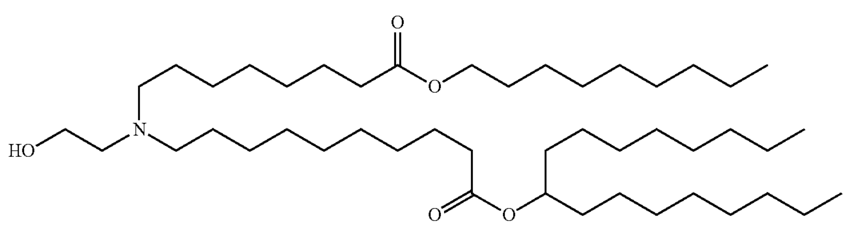 [SMILES: CCCCCCCCCOC(=O)CCCCCCCN(CCO)CCCCCCCCCC(=O)OC(CCCCCCCC)CCCCCCCC] | Synthesized in Example 1 Compound 23 in CN110520409A |
| Compound 25 | 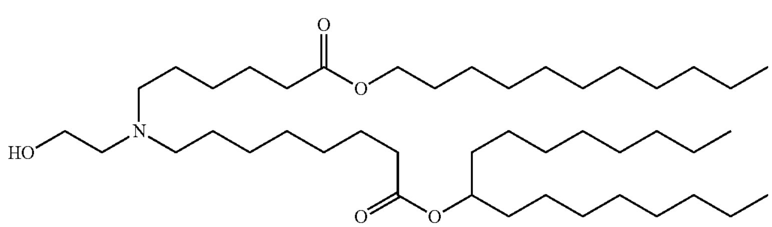 [SMILES: CCCCCCCCCCCOC(=O)CCCCCN(CCO)CCCCCCCC(=O)OC(CCCCCCCC)CCCCCCCC] | purchased from XiaMen Sinopeg Biotech Co., LTD., Compound 25 in CN110520409A |
| Compound 27 | 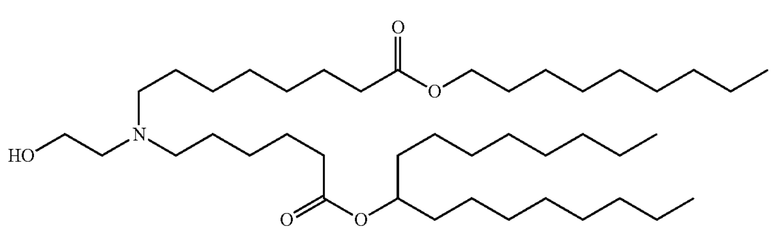 [SMILES: CCCCCCCCCOC(=O)CCCCCCCN(CCO)CCCCCC(=O)OC(CCCCCCCC)CCCCCCCC] | Synthesized in Example 1, Compound 27 CN110520409A |

TABLE 1-continued

Structure of cationic lipids

| Name | Structure | Remark |
|---|---|---|
| MC3 | [chemical structure] | purchased from XiaMen Sinopeg Biotech Co., LTD. |

The cationic lipids listed in Table 1 were dissolved in ethanol with DSPC (AVT (Shanghai) Pharmaceutical Technology Co., Ltd.), cholesterol (AVT (Shanghai) Pharmaceutical Technology Co., Ltd.) and DMG-PEG2000 according to a molar ratio of 50:10:38.5:1.5, respectively, to prepare ethanol lipid solution. The ethanol lipid solution was quickly added to citrate buffer (pH=4~5) by ethanol injection method, and vortexed for 30 s for later use. eGFP-mRNA (purchased from Shanghai Biohub International Trade Co., Ltd) or Fluc-mRNA (purchased from Shanghai Biohub International Trade Co., Ltd) was diluted in citrate buffer (pH-4~5) to give an aqueous mRNA solution. A certain volume of liposome solution and mRNA aqueous solution were used to prepare liposomes at a weight ratio of total lipids to mRNA of 16:1. The mixtures were sonicated at 25° C. for 15 min (with an ultrasonic frequency of 40 kHz and an ultrasonic power of 800 W). The resulting liposomes were diluted to 10 times volume with PBS, and then ultrafiltered with a 300 KDa ultrafiltration tube to remove ethanol. Then the volume was fixed to a certain volume with PBS to give an LNP formulation encapsulating eGFP-mRNA or Fluc-mRNA using cationic lipid/DSPC/cholesterol/DMG-PEG2000 (50:10:38.5:1.5 in molar percentage).

Example 5: Determination of Particle Size and Polydispersity Index (PDI) of Lipid Nanoparticles The particle size and polydispersity index (PDI) were determined by dynamic light scattering using Malvern laser particle size analyzer.

10 μL of the liposome solution was weighed, diluted to 1 mL with RNase-free deionized water, and added to the sample pool. Each sample was measured in triplicate. The measurement conditions were: 90° scattering angle, and 25° C. The test results were as follows:

TABLE 2

Particle size and polydispersity index (PDI)

| Name | Particle size (nm) | PDI (%) |
|---|---|---|
| YK-001 | 164.03 | 10.2 |
| YK-002 | 156.70 | 27.7 |
| YK-003 | 119.91 | 21.3 |
| YK-004 | 190.65 | 9.7 |
| YK-005 | 148.75 | 17.3 |
| YK-006 | 125.35 | 22.9 |
| YK-007 | 178.06 | 13.6 |
| YK-008 | 205.00 | 24.4 |
| YK-009 | 136.44 | 18.2 |
| YK-010 | 124.46 | 19.8 |
| YK-011 | 173.16 | 21.2 |
| Compound 23 | 114.12 | 24.4 |
| Compound 25 | 117.10 | 23.1 |
| Compound 27 | 178.85 | 13.6 |
| MC3 | 205.20 | 18.3 |

The lipid nanoparticles prepared in Example 4 had a particle size between 110 and 210 nm, and all the lipid nanoparticles could be used to deliver mRNA, wherein the particles prepared by compound 23 and YK-003 had the smallest particle sizes, which were 114.12 nm and 119.91 nm, respectively, and the particles prepared by YK-008 and MC3 had the largest particle sizes, which were 205.00 nm and 205.20 nm, respectively. All the lipid nanoparticles had a polydispersity index between 5% and 30%, wherein YK-004 had the smallest polydispersity index of 9.7%, and YK-002 had the largest polydispersity index of 27.7%.

Example 6: In Vitro Verification of the Performance of LNP Delivery Carriers

Cell recovery and passage: the method was the same as in Example 3.

Seeding plate: the method was the same as in Example 3.
1. Fluorescent Detection of Fluc-mRNA A LNP formulation containing 0.3 μg of Fluc-mRNA (the carrier components of the LNP formulation were cationic lipid, neutral lipid, structured lipid and polymer-conjugated lipid with a molar ratio of 50:10:38.5:1.5, wherein the cationic lipid was listed in Table 1) was added to the cell culture medium of a 96-well plate, and further incubated for 24 hours. The corresponding reagent was added according to the instructions of the Gaussia Luciferase Assay Kit, and the fluorescence expression intensity of each well was detected by an IVIS fluorescence detection system. This test verified the transfection efficiency of LNP formulations in cells. The results are shown in Table 3.

In order to further compare the intracellular transfection efficiency of LNP formulations prepared from cationic lipid YK-009 and compound 25, we prepared LNP formulations with Fluc-mRNA contents of 0.3 μg, 0.225 μg, 0.15 μg and 0.075 μg, respectively (the carrier components of the LNP formulation were cationic lipid, neutral lipid, structured lipid and polymer-conjugated lipid with a molar ratio of 50:10:38.5:1.5, wherein the cationic lipid was YK-009 or compound 25). The intracellular transfection activity of the prepared LNP formulations was detected, and the detection method was the same as above. The results are shown in Table 4.

TABLE 3

Results of fluorescence detection of Fluc-mRNA

| Serial No. | Cationic lipid | Relative light unit (RLU) | Times relative to compound 23 |
|---|---|---|---|
| 1 | YK-001 | 2243585 | 3.4 |
| 2 | YK-002 | 1284254 | 2.0 |
| 3 | YK-003 | 346698 | 0.5 |
| 4 | YK-004 | 138599 | 0.2 |
| 5 | YK-005 | 1444202 | 2.2 |
| 6 | YK-006 | 2714015 | 4.1 |

TABLE 3-continued

Results of fluorescence detection of Fluc-mRNA

| Serial No. | Cationic lipid | Relative light unit (RLU) | Times relative to compound 23 |
|---|---|---|---|
| 7 | YK-007 | 471960 | 0.7 |
| 8 | YK-008 | 1259555 | 1.9 |
| 9 | YK-009 | 5479373 | 8.4 |
| 10 | YK-010 | 93801 | 0.1 |
| 11 | YK-011 | 285918 | 0.4 |
| 12 | Compound 23 | 654930 | 1.0 |
| 13 | Compound 27 | 414334 | 0.6 |
| 14 | MC3 | 129292 | 0.2 |

TABLE 4

Fluorescence detection results of different Fluc-mRNA contents

| Fluc-mRNA content (μg) | Cationic lipid | Relative light unit (RLU) |
|---|---|---|
| 0.3 | Compound 25 | 1461700 |
|  | YK-009 | 5479373 |
| 0.225 | Compound 25 | 1296275 |
|  | YK-009 | 5234354 |
| 0.15 | Compound 25 | 530850 |
|  | YK-009 | 3725475 |
| 0.075 | Compound 25 | 325425 |
|  | YK-009 | 1444785 |

Figure 5:
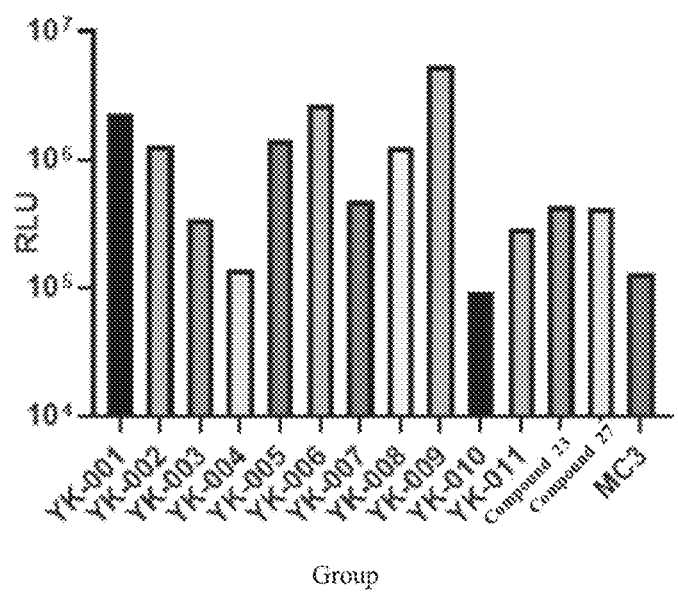
FIG. 5 shows the fluorescence absorption intensity of LNP formulations of Fluc-mRNA prepared from different cationic lipids.

It can be seen from Table 3 and FIG. 5 that among the LNP formulations of Fluc-mRNA prepared from different cationic lipids, YK-009 had the strongest fluorescence absorption with a RLU value of 5479373; YK-001, YK-002, YK-005, YK-006 and YK-008 also had very strong fluorescence absorption, all of which were between 106 and 107; and the RLU values of YK-009, YK-006, YK-001, YK-005, YK-002 and YK-008 were 8.4 times, 4.1 times, 3.4 times, 2.2 times, 2.0 times, and 1.9 times that of compound 23, respectively; YK-010 had the weakest fluorescence absorption with a RLU value of 93801; YK-004, compound 23, compound 27 and MC3 also had very weak fluorescence absorption, and the RLU values of YK-009 were 58 times, 39 times, 8 times, 13 times and 42 times that of YK-010, YK-004, compound 23, compound 27 and MC3, respectively.

Figure 6:
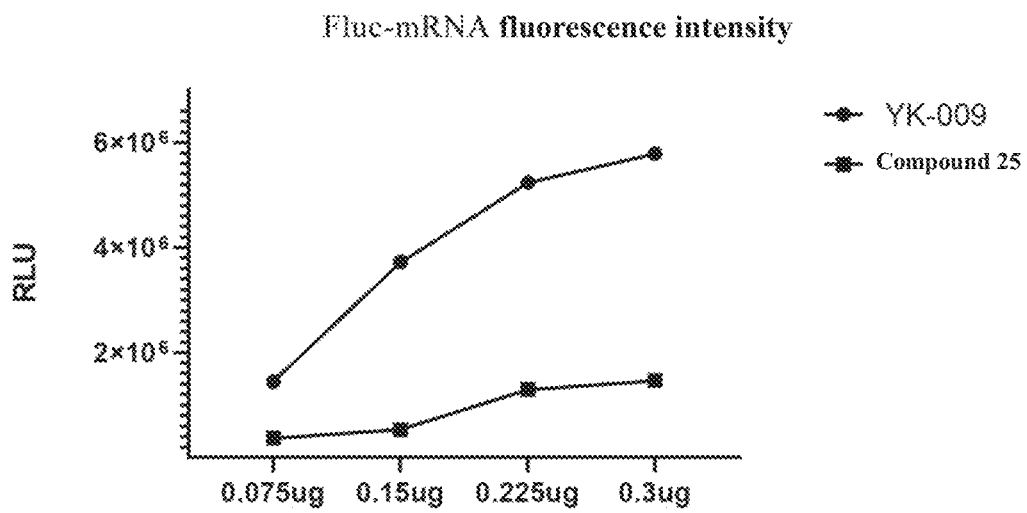
FIG. 6 shows the fluorescence absorption intensity of LNP formulations of Fluc-mRNA prepared respectively by cationic lipid YK-009 and compound 25, wherein the Fluc-mRNA content is 0.075 μg, 0.15 μg, 0.225 μg, and 0.3 μg, respectively.

It can be seen from Table 4 and FIG. 6 that LNP formulations prepared by YK-009 and compound 25 had very different fluorescence absorption, and for LNP formulations containing 0.075 μg, 0.15 μg, 0.225 μg and 0.3 μg of Fluc-mRNA, the fluorescence absorption of the YK-009 formulation was 3.7 times, 4.0 times, 7.0 times and 4.4 times that of the compound 25 formulation, respectively.

The data were analyzed with GraphPad Prism software, wherein the data of YK-009, YK-006, YK-001, YK-005, YK-002 and YK-008 were significantly different from those of compound 23, and the data of YK-009, YK-006, YK-001, YK-005, YK-002 and YK-008 were significantly different from those of compound 27. Except for YK-004 and YK-010, the data of all compounds were significantly different from those of MC3; for LNP formulations containing 0.075 μg, 0.15 μg, 0.225 μg and 0.3 μg of Fluc-mRNA, the data of YK-009 was significantly different from those of compound 25.

From the structural point of view, compared with YK-009, the $L_1$ group of YK-001 has one more C, and the other structures are exactly identical; the $G_1$ group of YK-002 has one more C, and the other structures are exactly identical; the $G_2$ group of YK-004 has two less C, and the other structures are exactly identical; the $G_2$ group of YK-006 has one less C, and the other structures are exactly identical; the two chains of the $L_2$ group of YK-010 each have one less C, and the other structures are exactly identical; compound 23 has four more C in the G1 group, one less C in the $L_1$ group, four more C in the $G_2$ group, and one less C in the single chain of the $L_2$ group, and the other structures are exactly identical; compound 25 has two more C in the $G_1$ group, one more C in the $L_1$ group, two more C in the $G_2$ group, and one less C in the single chain of the $L_2$ group, and the other structures are exactly identical; compound 27 has four more C in the $G_1$ group, one less C in the $L_1$ group, and one less C in the single chain of the $L_2$ group, and the other structures are exactly identical.

It can be seen that there is no corresponding relationship between the structure of the compound and the intracellular transfection efficiency, and the compounds with small structural differences may have a high probability of very large difference in transfection efficiency. For example, compared with YK-009, the structures of YK-010, YK-004, compound 23 and compound 27 are only slightly different, but the cell transfection efficiency of YK-009 was 58 times, 39 times, 8 times and 13 times that of these cationic lipid compounds, respectively. There is only a small difference in the structure between YK-009 and compound 25, but the difference in cell transfection efficiency can be 7 times. Therefore, it is not that compounds with similar structures must have similar transfection efficiencies, but are likely to have greatly different transfection efficiencies. Screening out cationic lipid compounds with high transfection efficiency is not easy, and requires various designs and a lot of creative work.

2. Cell Survival Rate Assay

A LNP formulation containing 1.5 μg of Fluc-mRNA (the carrier component of the LNP formulation was cationic lipid, neutral lipid, structured lipid and polymer-conjugated lipid with a molar ratio of 50:10:38.5:1.5, wherein the cationic lipid was listed in Table 1) was added to the cell culture medium of a 96-well plate, and further cultivated for 24 hours. 10 μL of CCK-8 solution was then added to each well, and the culture plate was incubated in an incubator for 1 hour. The absorbance at 450 nm was measured by a microplate reader. The results are shown in Table 4.

To compare the cytotoxicity of LNP formulations prepared from cationic lipid YK-009 and compound 25, we prepared LNP formulations with Fluc-mRNA contents of 1.5 μg, 1.125 μg, 0.75 μg and 0.375 μg (the carrier components of LNP formulations were cationic lipid, neutral lipid, structured lipid and polymer-conjugated lipid with a molar ratio of 50:10:38.5:1.5, wherein the cationic lipid was YK-009 or compound 25). The assay method of cell survival rate was the same as above. The results are shown in Table 6.

TABLE 5

Cell survival rate

| Serial No. | Cationic lipid | Cell survival rate (%) |
|---|---|---|
| 1 | YK-001 | 85 |
| 2 | YK-002 | 89 |
| 3 | YK-003 | 84 |
| 4 | YK-004 | 87 |
| 5 | YK-005 | 88 |
| 6 | YK-006 | 96 |
| 7 | YK-007 | 96 |
| 8 | YK-008 | 91 |
| 9 | YK-009 | 100 |
| 10 | YK-010 | 77 |

TABLE 5-continued

Cell survival rate

| Serial No. | Cationic lipid | Cell survival rate (%) |
|---|---|---|
| 11 | YK-011 | 98 |
| 12 | Compound 23 | 87 |
| 13 | Compound 27 | 84 |
| 14 | MC3 | 88 |

TABLE 6

Cell survival rate with different Fluc-mRNA contents

| Fluc-mRNA content (μg) | Cationic lipid | Cell survival rate (%) |
|---|---|---|
| 1.5 | Compound 25 | 91 |
|  | YK-009 | 100 |
| 1.125 | Compound 25 | 95 |
|  | YK-009 | 100 |
| 0.75 | Compound 25 | 97 |
|  | YK-009 | 100 |
| 0.375 | Compound 25 | 99 |
|  | YK-009 | 100 |

Figure 7:
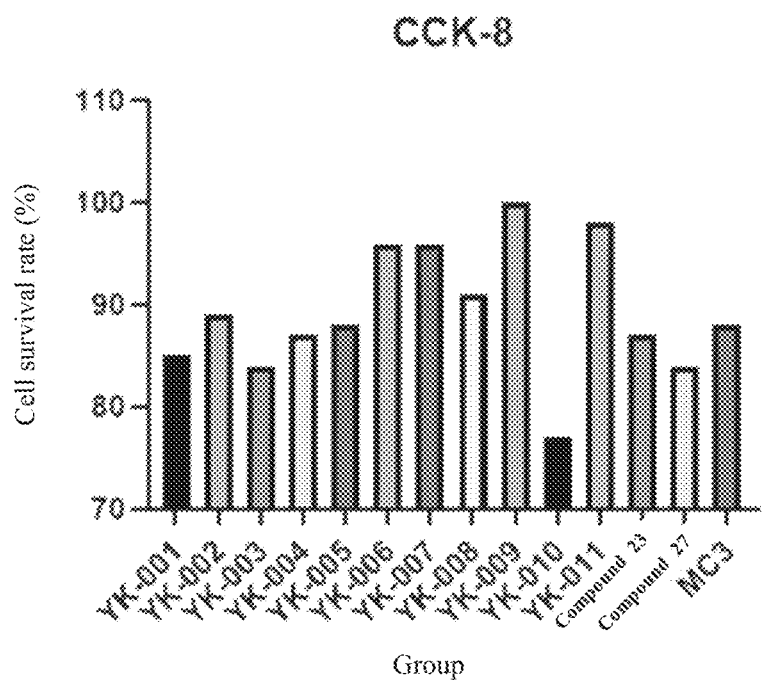
FIG. 7 shows the cell survival rate after introducing the LNP formulations of Fluc-mRNA prepared from different cationic lipids into the cell culture medium and culturing for 24 hours.

It can be seen from Table 5 and FIG. 7 that the LNP formulations of Fluc-mRNA prepared by different cationic lipids had very different cytotoxicity, wherein in terms of the cell survival rate, YK-009 was the highest, which was 100%, and YK-011 was 98%; however, YK-010 was 77%, YK-003 was 84%, YK-001 was 85%, compound 23 was 87%, compound 27 was 84%, and MC3 was 88%; these were obviously lower than YK-009.

Figure 8:
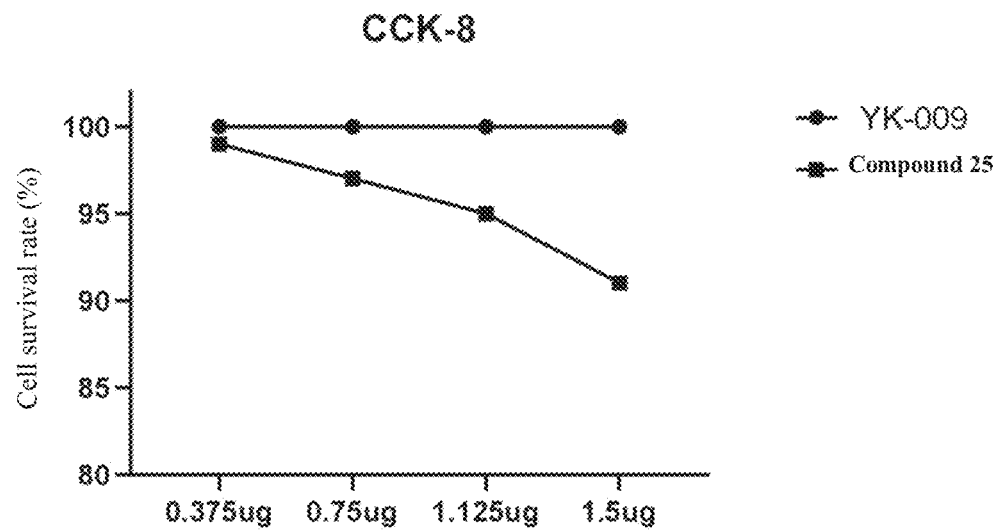
FIG. 8 shows the cell survival rate after introducing the LNP formulations (the content of Fluc-mRNA was 0.375 μg, 0.75 μg, 1.125 μg and 1.5 μg, respectively) of Fluc-mRNA prepared from cationic lipid YK-009 and compound 25 into the cell culture medium and culturing for 24 hours.

It can be seen from Table 6 and FIG. 8 that the LNP formulations prepared by YK-009 and compound 25 had very different inhibitory activities on cells, wherein for the LNP formulations with a Fluc-mRNA content of 1.5 μg, 1.125 μg, 0.75 μg and 0.375 μg, the cell survival rate of all the YK-009 formulations was 100%, and the inhibitory activity of compound 25 formulations on cells was up to 9% lower than that of YK-009 formulations.

The data were analyzed with GraphPad Prism software, and YK-009, YK-011, YK-006 and YK-007 had significant differences in cytotoxicity from compound 23, compound 27 and MC3.

From the above test results, it can be seen that there is no corresponding relationship between the structure of cationic lipid compounds and their cytotoxicity, and compounds with small structural differences may have great differences in cytotoxicity. For example, compared with YK-009, YK-010 having one less C in each of the two chains of the $L_2$ group with the other structures exactly identical, but had reduction in the cell survival rate by 23%; YK-002 having one more C in the $G_1$ group with the other structures exactly identical, but had reduction in the cell survival rate by 11%; compound 23 having four more C in the $G_1$ group, one less C in the $L_1$ group, four more C in the $G_2$ group, one less C in the single chain of the $L_2$ group with the other structures exactly identical, but had reduction in the cell survival rate by 13%; compound 25 having two more C in the $G_1$ group, one more C in the $L_1$ group, two more C in the $G_2$ group, one less C in the single chain of the $L_2$ group with the other structures exactly identical, but had reduction in the cell survival rate by 9%. Compound 27 having four more C in the $G_1$ group, one less C in the $L_1$ group, one less C in the single chain of the $L_2$ group with the other structures exactly identical, but had reduction in the cell survival rate by 16%. Although YK-009 is similar in structure to YK-010, YK-002, compound 23, compound 27 and compound 25, its cytotoxicity was 23%, 11%, 13%, 16% and 9% less, respectively. It can be seen that structurally small differences in cationic lipids may result in markedly different cytotoxicity.

Example 7: In Vivo Verification of Performance of Cationic Lipid (LNP) Delivery Carriers In addition, we also verified the protein expression and duration of mRNA delivered by our designed cationic lipid delivery carrier into mice. In vivo tests further proved that our LNP delivery carrier can effectively deliver mRNA into the body and express it efficiently and sustainably.

A LNP formulation containing 10 μg of Fluc-mRNA was intramuscularly injected into female BALB/C mice aged 4-6 weeks and weighing 17-19 g, and at specific time points (3 h, 6 h, 24 h, 48 h and 72 h) after administration, mice were injected intraperitoneally with a fluorescent imaging substrate. The mice moved freely for 5 minutes, and then the average radiation intensity (corresponding to fluorescence expression intensity) of the protein expressed by the mRNA carried by LNP in mice was detected using the IVIS Spectrum small animal live imager. The test results are shown in Table 5 and FIG. 7.

To compare the protein expression and duration in mice of LNP formulations prepared from cationic lipid YK-009 and compound 25, we prepared LNP formulations with Fluc-mRNA contents of 10 μg, 7.5 μg, 5 μg and 2.5 μg (the carrier components of LNP formulations were cationic lipid, neutral lipid, structured lipid and polymer-conjugated lipid with a molar ratio of 50:10:38.5:1.5, wherein the cationic lipid was YK-009 or compound 25). The mouse live imaging test method was the same as above. The results are shown in Table 8.

TABLE 7

Data of mouse live imaging test

| | Time | | | | |
|---|---|---|---|---|---|
| Cationic lipid | 3 h | 6 h | 24 h | 48 h | 72 h |
| YK-003 | 1500820 | 770220 | 527800 | 128720 | 39538 |
| YK-004 | 69640 | 40100 | 16080 | 4236 | 2066 |
| YK-009 | 1234280 | 976000 | 757440 | 135420 | 29435 |
| YK-010 | 60100 | 42520 | 15180 | 4676 | 810.2 |
| Compound 23 | 554600 | 766540 | 142800 | 19746 | 4801 |
| Compound 27 | 632450 | 609570 | 195700 | 21765 | 5512 |
| MC3 | 126862 | 130678 | 28780 | 14140 | 6716 |

TABLE 8

Data of mouse live imaging test with different Fluc-mRNA contents

| Fluc-mRNA content (µg) | Cationic lipid | Time | | | | |
|---|---|---|---|---|---|---|
| | | 3 h | 6 h | 24 h | 48 h | 72 h |
| 10 | Compound 25 | 654600 | 666540 | 140130 | 19065 | 4768 |
| | YK-009 | 1234280 | 976000 | 757440 | 135420 | 29435 |
| 7.5 | Compound 25 | 436650 | 514410 | 109040 | 14809 | 3271 |
| | YK-009 | 925710 | 732000 | 568080 | 101565 | 22076 |
| 5 | Compound 25 | 342850 | 304240 | 68710 | 10417 | 2206 |
| | YK-009 | 617140 | 488000 | 378720 | 67710 | 14717 |
| 2.5 | Compound 25 | 192860 | 142520 | 35050 | 4993 | 1207 |
| | YK-009 | 308570 | 244000 | 189360 | 33855 | 7358 |

Figure 9:
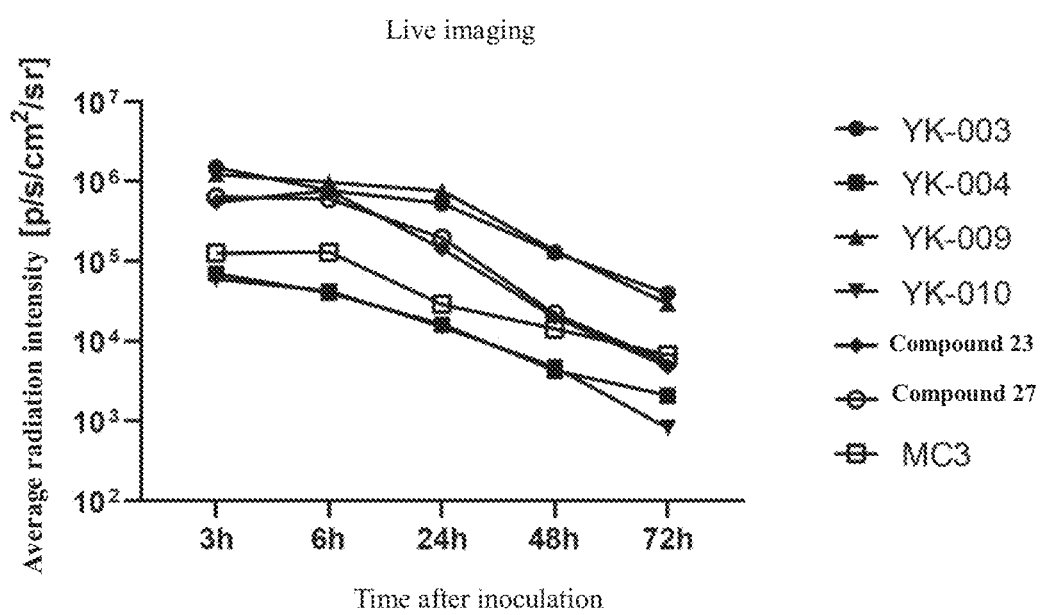
FIG. 9 shows the results of live mouse imaging tests of LNP formulations of Fluc-mRNA prepared from different cationic lipids.

It can be seen from Table 7 and FIG. 9 that the expression intensity of LNP formulations of Fluc-mRNA prepared from different cationic lipids varied greatly in mice. From 3 h to 72 h, YK-003 and YK-009 had the highest expression intensity, indicating that the LNP formulations prepared from them were highly and sustainably expressed in vivo; at 3 hours, the average radiation intensity of YK-003 and YK-009 was 1500820 and 1234280, respectively; YK-004 and YK-010 were the lowest, being 69640 and 60100, respectively; the mRNA carried by the four differed by more than 20 times between the highest and the lowest Fluc-mRNA expressions in animals; at 72 hours, the average radiation intensities of YK-003 and YK-009 were 39538 and 29435 respectively, and the lowest was YK-004 and YK-010 with average radiation intensities of 2066 and 810.2, respectively; the difference between the highest and lowest expression of mRNA carried by the four in animals was up to 50 times. The average radiation intensities of compounds 23 and 27 were 554600 and 632450 at 3 h, respectively, but decreased rapidly between 6 h and 48 h, and were only 4801 and 5512 at 72 h, indicating that the mRNA carried by the LNP formulations prepared by them was quickly degraded or metabolized in mice. The expression of mRNA carried by MC3 was very low at each time, indicating that the mRNA carried by MC3 was lowly expressed in vivo, and the expression was not sustained.

Figure 10:
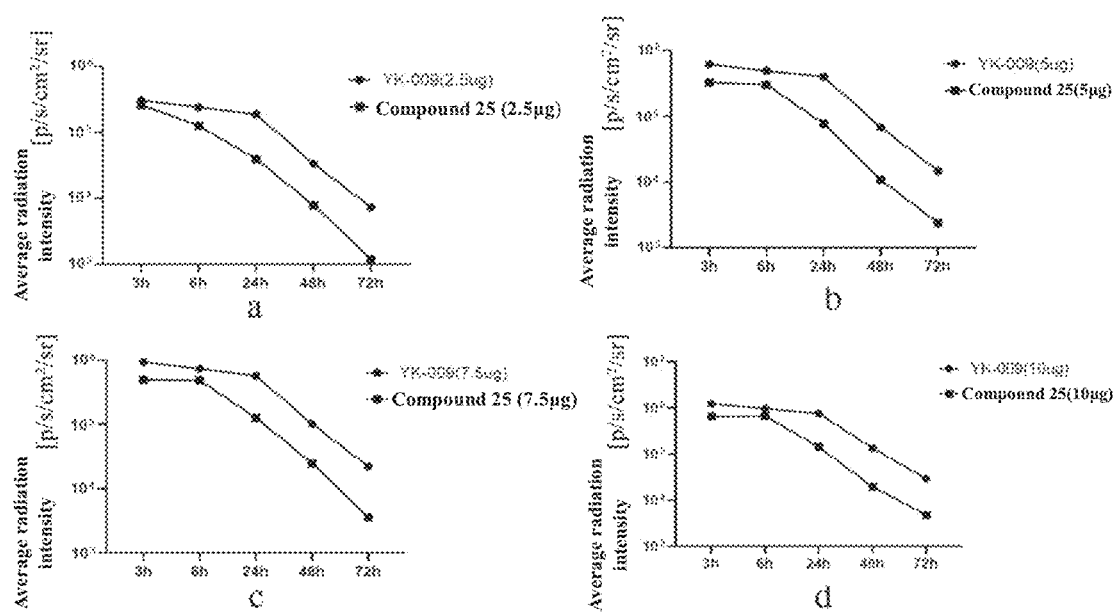
FIG. 10 shows the results of live mouse imaging tests of LNP formulations of Fluc-mRNA prepared by cationic lipid YK-009 and compound 25 respectively, wherein the LNP formulations have different Fluc-mRNA contents: a is 2.5 μg, b is 5 μg g, c is 7.5 μg, and dis 10 μg.

It can be seen from Table 8 and FIG. 10 that the LNP formulations prepared by YK-009 and compound 25 in mice had quite different expression. Regarding the LNP formulations with Fluc-mRNA contents of 2.5 µg, 5.0 µg, 7.5 µg and 10 µg, the expression for YK-009 was 1.6-2.1 times that for compound 25 at 3 hours, 1.4-1.7 times that for compound 25 at 6 hours, 5.2-5.5 times that for compound 25 at 24 hours, 6.5-7.1 times that for compound 25 at 48 hours, and 6.1-6.8 times that for compound 25 at 72 hours. For the LNP formulations with different Fluc-mRNA contents, all the YK-009 formulations can maintain high expression in vivo for a long time, and compound 25 formulations can maintain high expression at 3 h and 6 h, but decreased rapidly at 6~48 h.

Data were analyzed with GraphPad Prism software. In terms of high expression and sustained expression of mRNA carried by LNP in animals, YK-003 and YK-009 were significantly different from compound 23, compound 25, compound 27, and MC3.

From the above test results, it can be seen that there is no corresponding relationship between the structure of cationic lipid compounds and the high expression and sustained expression of mRNA carried by LNP in animals. Cationic lipid compounds with little structural difference may have great difference in promoting the expression of mRNA in mice. For example, compared with YK-009, YK-004 only has two less C in the $G_2$ group with the other structures exactly identical; YK-010 has one less C in each of the double chains of the $L_2$ group with the other structures exactly identical; compound 23 has four more C in the G group, one less C in the $L_1$ group, four more C in the $G_2$ group, one less C in the single chain of the $L_2$ group with the other structures exactly identical; compound 27 has four more C in the $G_1$ group, one less C in the $L_1$ group, one less C in the single chain of the $L_2$ group with the other structures exactly identical; but at 3 hours, the expression of the mRNA carried by the four in animals differed by more than 20 times between the highest and the lowest; and at 72 hours, the expression of the mRNA carried by the four in animals differed by up to 50 times between the highest and the lowest.

Compared with YK-009, compound 25 has two more C in the $G_1$ group, one more C in the $L_1$ group, two more C in the $G_2$ group, one less C in the single chain of the $L_2$ group with the other structures exactly identical; but regarding the LNP formulations prepared by YK-009 and compound 25 with Fluc-mRNA contents of 2.5 µg, 5.0 µg, 7.5 µg and 10 µg, the expression of the mRNA for YK-009 can be up to 2.1 times that for compound 25 at 3 hours, can be up to 1.7 times that for compound 25 at 6 hours, can be up to 5.5 times that for compound 25 at 24 hours, can be up to 7.1 times that for compound 25 at 48 hours, and YK-009 can be up to 7.2 times that for compound 25 at 72 hours.

IN CONCLUSION

The above in vitro and in vivo tests to verify the performance of LNP delivery carriers show that the structure of cationic lipid compounds has no apparent corresponding relationship with intracellular transfection efficiency, cytotoxicity, and high expression and sustained expression in animals. Compounds with very small structural difference may have very large difference in transfection efficiency and/or cytotoxicity and high expression in cells. For example, the compounds YK-009 and YK-010 of the present application differ nearly 60 times in cell transfection efficiency, and differ 25% or more in toxicity to transfected cells; and compounds YK-003 and YK-010 differ in the expression and sustained expression in mice up to 50 times. Therefore, it is very difficult to screen out suitable cationic lipid compounds that can simultaneously have high transfection efficiency, low cytotoxicity, and high and sustained expression in mice.

The present application found some compounds, such as YK-009, YK-003, YK-006, YK-008 and YK-011, through unique design and a large number of screenings. Compared with other compounds in the prior art, these compounds can deliver nucleic acids with high cell transfection efficiency, low or no cytotoxicity, and high and sustained expression in animals, achieving unexpected technical effects.

The above descriptions are only exemplary embodiments of the present disclosure, and are not intended to limit the protection scope of the present disclosure, which is determined by the appended claims.

The invention claimed is:

1. A compound, or an N-oxide, solvate, pharmaceutically acceptable salt or stereoisomer thereof, wherein the compound is:

YK-009

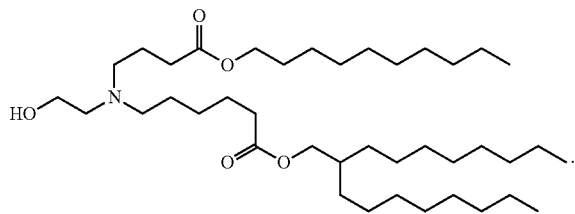

2. A composition comprising a carrier, wherein the carrier comprises a cationic lipid, and the cationic lipid contains the compound or an N-oxide, solvate, pharmaceutically acceptable salt or stereoisomer thereof according to claim 1.

3. The composition according to claim 2, wherein the carrier further comprises a neutral lipid.

4. The composition according to claim 3, wherein the neutral lipid comprises one or more of phosphatidylcholine, phosphatidylethanolamine, sphingomyelin, ceramide, sterol and a derivative thereof, alternatively, the neutral lipid is selected from one or more of 1,2-dilinoleoyl-sn-glycero-3-phosphocholine (DLPC), 1,2-dimyristoyl-sn-glycero-phosphocholine (DMPC), 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-dioleoyl-sn-glycero-3-phosphoethanolamine (DOPE), 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), dipalmitoyl phosphatidylglycerol (DPPG), palmitoyl oleoyl phosphatidylethanolamine (POPE), distearoyl-phosphatidyl-ethanolamine (DSPE), dipalmitoyl phosphatidylethanolamine (DPPE), dimyristoyl phosphoethanolamine (DMPE), 1-stearyl-2-oleoyl-stearoylethanolamine (SOPE), 1-stearoyl-2-oleoyl-phosphatidylcholine (SOPC), sphingomyelin, phosphatidylcholine, phosphatidylethanolamine, phosphatidylserine, phosphatidylinositol, phosphatidic acid, palmitoyl oleoyl phosphatidylcholine, lysophosphatidylcholine, lysophosphatidylethanolamine (LPE), and mixtures thereof.

5. The composition according to claim 2, wherein the carrier further comprises a structured lipid.

6. The composition according to claim 5, wherein the structured lipid is selected from one or more of cholesterol, nonsterol, sitosterol, ergosterol, campesterol, stigmasterol, brassicasterol, tomatine, tomatine, ursolic acid, alpha-tocopherol, and corticosteroid.

7. The composition according to claim 2, wherein the carrier further comprises a polymer-conjugated lipid.

8. The composition according to claim 7, wherein the polymer-conjugated lipid is selected from one or more of PEG-modified phosphatidylethanolamine, PEG-modified phosphatidic acid, PEG-modified ceramide, PEG-modified dialkylamine, PEG-modified diacylglycerol, and PEG-modified dialkylglycerol.

9. The composition according to claim 2, wherein the carrier further comprises a neutral lipid, a structured lipid and a polymer-conjugated lipid, and the molar ratio of the cationic lipid, the neutral lipid, the structured lipid and the polymer-conjugated lipid is (25-65):(5-25):(25-45):(0.5-5).

10. The composition according to claim 2, wherein the composition is a nanoparticle formulation which has an average particle size of 10 nm to 210 nm and a polydispersity coefficient less than or equal to 50%.

11. The composition according to claim 2, wherein the cationic lipid further comprises one or more other ionizable lipid compound(s).

12. The composition according to claim 2, further comprising a therapeutic or prophylactic agent.

13. The composition according to claim 12, wherein the therapeutic or prophylactic agent comprises one or more of a nucleic acid molecule, a small molecule compound, a polypeptide or a protein.

14. The composition according to claim 13, wherein the therapeutic or prophylactic agent is ribonucleic acid (RNA) or deoxyribonucleic acid (DNA).

15. The composition according to claim 12, wherein the composition further comprises one or more of pharmaceutically acceptable excipients or diluents.

16. A method of treating a disease or condition characterized by dysfunctional or abnormal protein or polypeptide activity in a mammal in need thereof, comprising administrating the mammal the composition according to claim 12.

17. The method according to claim 16, wherein the disease or condition is selected from the group consisting of infectious diseases, cancer and proliferative diseases, genetic diseases, autoimmune diseases, diabetes, neurodegenerative diseases, cardiovascular and renovascular diseases, and metabolic diseases.

18. The method according to claim 17, wherein the infectious disease is selected from: diseases caused by coronavirus, influenza virus or HIV virus, infantile pneumonia, Rift Valley fever, yellow fever, rabies, and various herpes.

19. The method according to claim 16, wherein the composition is administered intravenously, intramuscularly, intradermally, subcutaneously, intranasally or by inhalation.

20. The method according to claim 16, wherein the therapeutic or prophylactic agent is administered to the mammal at a dose of about 0.001 mg/kg to about 10 mg/kg.

21. The composition according to claim 2, wherein the molar ratio of the cationic lipid to the carrier is from 30% to 70%.

22. The composition according to claim 5, wherein the molar ratio of the cationic lipid to the structured lipid is from 1:1 to 5:1.

23. The composition according to claim 6, wherein the structured lipid is cholesterol.

24. The composition according to claim 7, wherein the molar ratio of the polymer-conjugated lipid to the carrier is from 0.5% to 5%.

25. The composition according to claim 8, wherein the polymer-conjugated lipid is selected from one or more of distearoyl phosphatidylethanolamine polyethylene glycol 2000 (DSPE-PEG2000), dimyristoylglycero-3-methoxy polyethylene glycol 2000 (DMG-PEG2000) and methoxy-polyethylene glycol ditetradecylacetamide (ALC-0159).

26. The composition according to claim 9, wherein the molar ratio of the cationic lipid, the neutral lipid, the structured lipid, and the polymer-conjugated lipid is 50:10:38.5:1.5.

27. The composition according to claim 10, wherein the polydispersity coefficient is less than or equal to 30%.

28. The composition according to claim 13, wherein the therapeutic or prophylactic agent is a vaccine or compound capable of eliciting an immune response.

29. The composition according to claim 14, wherein the therapeutic or prophylactic agent is selected from the group consisting of small interfering RNA (siRNA), asymmetric interfering RNA (aiRNA), microRNA (miRNA), Dicer-substrate RNA (dsRNA), small hairpin RNA (shRNA), messenger RNA (mRNA), and mixtures thereof.

30. The composition according to claim 3, wherein the molar ratio of the cationic lipid to the neutral lipid is from 1:1 to 10:1.

31. The composition according to claim 4, wherein the neutral lipid is DOPE and/or DSPC.

32. The composition according to claim 12, wherein the mass ratio of the carrier to the therapeutic agent or prophylactic agent is from 10:1 to 30:1.

\* \* \* \* \*